United States Patent [19]

Mandelis et al.

[11] Patent Number: 5,667,300
[45] Date of Patent: Sep. 16, 1997

[54] NON-CONTACT PHOTOTHERMAL METHOD FOR MEASURING THERMAL DIFFUSIVITY AND ELECTRONIC DEFECT PROPERTIES OF SOLIDS

[76] Inventors: Andreas Mandelis, 3 Scarborough Heights Blvd., Scarborough, Ontario, Canada, M1M 2V3; Mahendra Munidasa, 152 Homestead Road Unit 25, Scarborough, Ontario, Canada, M1E 3S2

[21] Appl. No.: 264,164

[22] Filed: Jun. 22, 1994

[51] Int. Cl.[6] ................................................. G01N 25/20
[52] U.S. Cl. ............................. 374/43; 374/121; 374/128
[58] Field of Search ............................... 374/43, 44, 121, 374/128, 45; 364/498, 576, 572, 483, 557; 250/341.6

[56] References Cited

U.S. PATENT DOCUMENTS

| | | | |
|---|---|---|---|
| 4,933,887 | 6/1990 | Danko et al. | 374/45 |
| 4,944,590 | 7/1990 | Poisel et al. | 356/350 |
| 4,950,990 | 8/1990 | Moulder et al. | 374/45 |
| 4,965,451 | 10/1990 | Solter | 374/4 |
| 5,020,920 | 6/1991 | Gopalsami et al. | 374/45 |
| 5,047,713 | 9/1991 | Kirino et al. | 374/4 |
| 5,099,441 | 3/1992 | Mazzio | 374/44 |

*Primary Examiner*—William A. Cuchlinski, Jr.
*Assistant Examiner*—Andrew Hirshfeld
*Attorney, Agent, or Firm*—Staas & Halsey

[57] ABSTRACT

There is provided a method of measuring thermal diffusivity of solids and electronic lifetimes and defect properties of semiconductors useful for in-situ, non-destructive monitoring of engineered materials and electronic substrates. The method, termed photothermal rate window method, involves irradiating a sample with a repetitive square laser pulse of duration $\tau_p$ and period $T_0$ and monitoring the temperature profile by measuring the photothermal signal emitted from the sample. The period $T_0$ of the repetitive heating pulse is maintained constant and the pulse duration $\tau_p$ is varied in the range between 0 and $T_0$ with the temperature measured at each value of $\tau_p$. The method of measuring semiconductor recombination lifetimes involves irradiating a sample and scanning one of either the period $T_0$ and the pulse duration $\tau_p$ of the repetitive laser pulse with the other held constant. The photothermal signal emitted from the surface is measured. Defect energy states in semiconductors are measured by irradiating the sample with a repetitive laser pulse of duration $\tau_p$ and period $T_0$ (both fixed) and monitoring the photothermal signal as the sample temperature is scanned. Defect levels are correlated with extremum in the profile. The photothermal signal in all the foregoing methods is input into a lock-in amplifier which measures the fundamental Fourier component of the signal. The output of the lock-in amplifier is fitted to a theoretical model of the photothermal response of a repetitively irradiated sample to obtain the thermal diffusivity, or the recombination lifetime.

19 Claims, 13 Drawing Sheets

NON-CONTACT PHOTOTHERMAL METHOD FOR MEASURING THERMAL DIFFUSIVITY AND ELECTRONIC DEFECT PROPERTIES OF SOLIDS

FIELD OF THE INVENTION

The present invention relates to a method for measuring thermal and electronic properties of solids, and more particularly relates to dynamical methods for measuring thermal diffusivity of solids such as metal foils, thermal diffusivities and carrier lifetimes of photoexcited carriers in semiconductors, and interband energy levels in semiconductors.

BACKGROUND OF THE INVENTION

The thermal conductivity k of a material is a measure of the ability of the material to conduct heat. The thermal diffusivity of a material $\alpha$, is related to the conductivity k by:

$$\alpha = k/\rho c$$

where $\rho$ is the density of the material and c is the specific heat capacity of the material. The product $\rho c$ is the thermal capacitance per unit volume of the material which generally does not vary significantly for materials from the same family such as different kinds of steels. The thermal capacitance per unit volume also generally does not vary appreciably with certain types of engineering processes such as surface hardening.

Thermal diffusivity of a material is a thermophysical parameter which gives direct and indirect information useful in for example modelling of various industrial processes. Specifically, direct knowledge of thermal diffusivity is required in the modelling of cooling and heating of machinery, heat sinks or spreaders and heat resistant coatings for example. Indirect information of thermal diffusivity obtained from thermal analysis is also useful in non-destructive depth profiling of surface modified metals, the curing of reaction-moulding resins and potentially in the in-situ quality control of manufactured metal sheet.

By measuring thermal diffusivity the thermal conductivity can be obtained using equation (1) using tabulated values of $\rho c$. Alternatively, measuring thermal conductivity allows calculation of thermal diffusivity. Typically, thermal conductivity of a material is measured using steady state heat flow methods and there are several experimental techniques currently in use. Experimental methods exist for measurement of thermal diffusivity using time-dependent or dynamic heat flow methods. Dynamic methods of measuring thermal diffusivity are in many ways superior to steady state conductivity measurements in that they allow for faster measurement of thermal diffusivity and are relatively insensitive to background fluctuations and boundary losses; see G. Busse and H. G. Walther, in *Progress in Photoacoustic and Photothermal Sciences and Technology*, edited by A. Mandelis, Vol. 1, Chapter 5, p. 205, (Elsevier, New York, 1991)].

There are essentially two dynamic or time dependent methods for measuring thermal diffusivity. The first is the periodic heat flow method (see for example L. Qian and P. Li, Appl. Opt. 29, 4241, 1990), and the second comprises transient methods as disclosed in W. P. Leung and A. C. Tam, J. Appl. Phys. 56, 153 (1984) and S. B. Peralta, S. C. Ellis, C. Christofides and A. Mandelis, J. Res. Non-Destructive Eval., 3, 69 (1991).

In the periodic heat flow case, a sample of known thickness is irradiated with a harmonically modulated laser beam thereby launching a thermal wave through the sample. The resulting periodic temperature profile at the front or back surface of the sample is monitored at several modulation frequencies f, also known as the frequency scan method. The frequency dependent thermal diffusion length $\mu$ is given by:

$$\mu = \sqrt{\alpha/\pi f}$$

and is related to the phase-lag of the detected temperature wave with respect to the heating source and may be monitored using a lock-in amplifier.

In transient measurement techniques such as pulsed or multi-frequency spectral excitation, a sample of known thickness is irradiated on one side with a laser pulse and the time evolution of the temperature on either side is monitored and the rate of decay of the temperature is related to the diffusivity.

The measurement of photoexcited excess carrier lifetime is useful in characterizing the quality of semiconductor materials and modelling semiconductor devices. Besides the conventional photoconductive technique for carrier lifetime measurement, many recently developed noncontact, nondestructive techniques have drawn particular interest, [D. K. Schroder, *Semiconductor Material and Device Characterization* (Wiley, New York, 1990); J. W. Orton and P. Blood, *The Electrical Characterization of Semiconductors: Measurement of Minority Carrier Properties* (Academic, San Diego, 1990)]. Photothermal radiometry (PTR), (S. J. Sheard, M. G. Somekh and T. Hiller, Mater. Sci. Eng. B 5, 101 (1990)], laser/microwave absorption/reflection (LMR), [T. Warabisako, T. Saitoh, T. Motooka and T. Tokuyama, Jpn. J. Appl. Phys. Suppl. 22-1, 557 (1982); J. Waldmeyer, J. Appl. Phys. 63, 1977 (1988); Z. G. Ling and P. K. Ajmera, J. Appl. Phys. 69, 519 (1991)], infrared absorption (IA), [Y. Mada, Jpn. J. Appl. Phys. 18, 2171 (1979); F. Shimura, T. Okui and T. Kusama, J. Appl. Phys. 61, 7168 (1990); A. Buczkowski, G. A. Rozgonyi and F. Shimura, Proc. MRS Spring Conf. (1992)], photoconductance (PC), [T. Tiegje, J. I. Haberman, R. W. Francis and A. K. Ghosh, J. Appl. Phys. 54, 2499 (1983)], or open-circuit voltage decay (OCVD), [U. Lehmann and H. Foll, J. Electrochem. Soc. 135, 2831 (1988)], are among those techniques commonly used for noncontact carrier lifetime studies. In all these methods laser illumination is used to generate excess electron-hole pairs. The resulting signal is detected in the frequency-domain as a function of modulation frequency (in PTR) or in the time-domain as a transient signal (IA, LMR, PC, and OCVD).

SUMMARY OF THE INVENTION

The present invention provides a method of noncontact measurement of thermal diffusivity, excess-charge carrier lifetimes and interbandgap energy levels in solids. In one aspect the present method comprises (a) providing a sample of the solid; (b) irradiating the solid with an excitation pulse of period $T_o$ and a pulse duration $\tau_{p1}$, whereby a photothermal signal is responsively emitted from said solid; (c) detecting said emitted photothermal signal and inputing said photothermal signal into a signal detection means operable to measure a fundamental Fourier component of said photothermal signal and provide an output of said fundamental Fourier component; and (d) fitting said output fundamental Fourier component to a theoretical model of the photothermal response of a repetitively irradiated solid to obtain at least one of the thermal diffusivity, excess charge carrier lifetimes and interbandgap defect impurity energy levels in the solid.

The present invention provides a method of measuring thermal diffusivity of a solid comprising the steps of (a) providing a sample of the solid; (b) irradiating the solid with a periodic heat generating signal having a fixed period $T_o$ and a predetermined pulse duration $\tau_p$ in a range from about zero to $T_o$, whereby a photothermal signal is produced; (c) detecting said photothermal signal; (d) processing said photothermal signal using a signal processing means to measure a fundamental Fourier component of the photothermal signal and calculate a quadrature component of said fundamental Fourier component, and correcting said quadrature component for frequency dependent shifts due to said signal processing means to give an output quadrature value at said pulse duration $\tau_p$; (e) changing the pulse duration $\tau_p$ to a new value in said range and repeating steps (b) to (d); (f) repeating step (e) until said range has been scanned by the pulse duration $\tau_p$; and (g) fitting said output quadrature value to a theoretical model of the photothermal response of a repetitively irradiated solid to obtain the thermal diffusivity of the solid.

In another aspect of the subject invention, in a semiconductor having an energy bandgap, there is provided a method of measuring energy levels in said energy bandgap arising from defect or impurities in the semiconductor. In this aspect of the invention the method comprises (a) bringing said semiconductor to a first temperature in a predetermined temperature range; (b) irradiating the semiconductor with a light pulse having a predetermined pulse duration $\tau_p$ and repetition period $T_0$, the light pulse having a wavelength suitable to produce photoexcited electronic carriers, whereby after the light pulse is switched off decay of said photoexcited electronic carriers occurs at the defect or impurity sites to release energy thereby causing a temporary peak in the temperature of the semiconductor responsively producing a photothermal signal; (c) detecting said photothermal signal and inputing said photothermal signal into a lock-in amplifier which measures the fundamental Fourier component of said photothermal signal and provides an output signal; (d) bringing the temperature of said semiconductor to a new temperature in said predetermined temperature range and repeating steps (b) to (e) until a photothermal spectrum has been produced spanning said predetermined temperature range and determining if any extrema are present in said photothermal spectrum; and correlating said extreme with the defect or impurity energy levels in said energy bandgap.

The present invention provides a method of noncontact measurement of thermal diffusivity and excess charge carrier lifetimes in semiconductors having a charge carrier system. This method comprises the steps of (a) providing a sample of the semiconductor; (b) irradiating the semiconductor with a light pulse having a pulse duration $\tau_p$ and repetition period $T_0$, whereby one of pulse duration $\tau_p$ and repitition period $T_0$ but not both are scanned while the other is maintained at a predetermined value, the light pulse having a wavelength suitable to produce photoexcited electronic carriers, whereby after the light pulse is switched off recombination of said photoexcited electronic carriers occurs to release energy thereby causing a temporary peak in the temperature of the semiconductor responsively producing an photothermal signal; (c) detecting said photothermal signal and inputing said photothermal signal into a signal detection means to measure a fundamental Fourier component of said photothermal signal and provide an output signal; and fitting said output signal to a theoretical model of the photothermal response of a repetitively irradiated semiconductor to obtain one of the thermal diffusivity and excess charge carrier lifetimes in the semiconductor.

BRIEF DESCRIPTION OF THE DRAWINGS

The method of the present invention will now be described, by way of example only, reference being had to the accompanying drawings in which:

FIG. 2b shows the observed (filled circles) frequency scanned amplitude data for the system of FIG. 2a;

FIG. 3b shows the observed (filled circles) frequency scanned amplitude data for the system of FIG. 3a;

Figure 1:
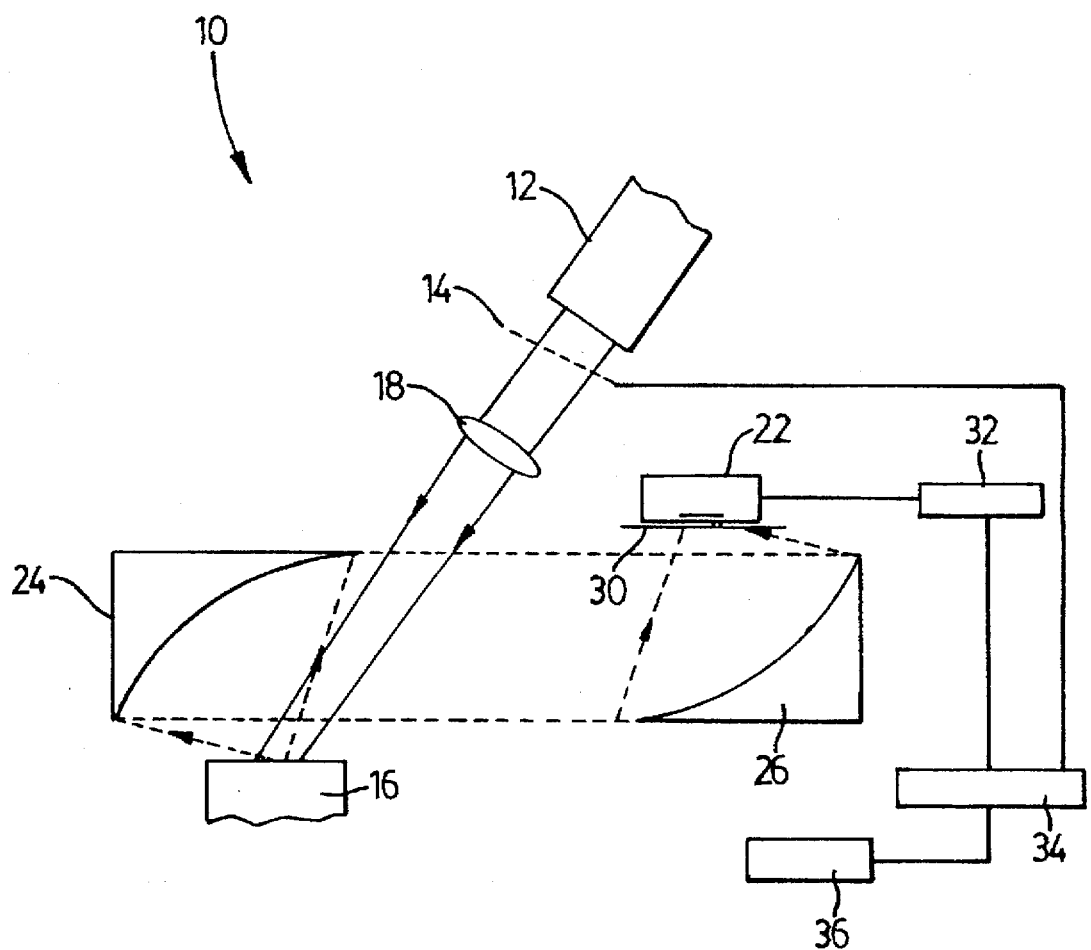
FIG. 1 illustrates a block diagram of one embodiment of an apparatus used for measuring thermal diffusivities, excess carrier lifetimes and impurity interbandgap energy levels according to the method of the present invention.

Prior Art i) Conventional Photothermal Frequency Scan Method

The difference between the rate window method of the present invention and the conventional frequency scan method is best understood by comparison of the two methods. The conventional frequency scan method will be first described followed by a description of the rate window method forming the present invention.

A one-dimensional analysis of the diffusion and reflection of the thermal wave generated by a laser beam modulated at angular frequency $\omega$, yields the following expression for the a.c. temperature at the irradiated surface:

$$T(\omega) = \frac{I_0 \eta_s}{k_s \sigma_s (1 + b_{gs})} \cdot \frac{1 + R_{gs} \exp(-2\sigma_s L)}{1 - R_{gs}^2 \exp(-2\sigma_s L)} \quad (1)$$

(see G. Busse and H. G. Walther, in *Progress in Photoacoustic and Photothermal Science and Technology*, edited by A. Mandelis, Vol. 1, Chapter 5, p. 205, (Elsevier, New York, 1991)) where L is the thickness and $k_s$ is the thermal conductivity of the sample; $I_o$ is the laser irradiance; $\eta_s$ is the optical-to-thermal energy conversion efficiency at the sample surface; and $b_{gs}$ is the thermal coupling coefficient to the surrounding gas (air) given by:

$$b_{gs} = \frac{k_g \sqrt{\alpha_g}}{k_s \sqrt{\alpha_s}}. \quad (2)$$

Here, $k_j$ is the thermal conductivity and $\alpha_j$ is the thermal diffusivity of medium (j) with the subscripts s and g referring to the sample and the gas, respectively. The quantity $R_{gs}$ given by:

$$R_{gs} = \frac{1 - b_{gs}}{1 + b_{gs}} \quad (3)$$

is the thermal-wave reflection coefficient at the solid-gas interface and $\sigma_s$ is a complex diffusion coefficient given by:

$$\sigma_s = (1+i)\sqrt{\frac{2\alpha_s}{\omega}}. \quad (4)$$

It is assumed that the solid and air are in perfect thermal contact. Expressions for the measured quantities, phase and magnitude, can be derived from the real and imaginary parts of Equation 1. The measurements are made with respect to a thermally thick (L>>μ) reference sample where the signal is given by:

$$T_{ref}(\omega) = \frac{I_0 \eta_r}{k_r \sigma_r (1 + b_{gr})}, \quad (5)$$

to compensate for the instrumental transfer function. For radiometric detection both T($\omega$) and $T_{ref}(\omega)$ expressions must be multiplied by terms including surface emissivity, detector parameters, ambient temperature, etc. This constant multiplicative term, except for the sample dependent terms, is cancelled out from the normalized signal Equation 1 divided by Equation 5.

By fitting the normalized experimental data (phase and magnitude) frequency dependence to the corresponding expressions derived from Equation 1, the parameters $R_{gs}$ and $L/(\alpha_s)^{1/2}$ can be calculated. Since the coupling medium is air [$k_g$=0.026 Wm$^{-1}$K$^{-1}$, $\alpha_g$=3.1×10$^{-5}$ m$^2$s$^{-1}$; A. Rosencwaig, *Photoacoustics and Photoacoustic Spectroscopy*, Chem. Anal. Vol. 57 (J. Wiley & Sons, New York, 1980), p. 96] the value of $b_{gs}$<<1. Therefore, $R_{gs}$ is almost unity and its sensitivity to $k_s$ is extremely small. That simplification makes $L/(\alpha_s)^{1/2}$ to be the only fitting parameter for normalized phase data. In addition to $L/(\alpha_s)^{1/2}$ the normalized amplitude data contain a multiplicative factor due to any differences in the bulk thermal properties and the surface finish between the sample and the reference. This factor may be cancelled out by setting the amplitude ratio to be unity at the high frequency (thermally thick) end where the phase difference is expected to be zero. Setting the amplitude ratio equal to unity is possible because we are only interested in the shape of the normalized curve, not in the absolute magnitude. Since there exists an extremum in the frequency curve of both magnitude and phase which is very sensitive to $L/(\alpha_s)^{1/2}$, it is not necessary to fit an entire frequency range. This could be used as a fast on-line measurement of small variations in L or $\alpha_s$ in an industrial environment.

ii) Conventional Photothermal Electronic Lifetime Measurement Methods

For some time now several laser-based photothermal techniques have been developed to monitor photoexcited carrier kinetics and transport in semiconductors, the advantage over other, mainly electrical, methods being that electronic effects can thus be monitored in a noncontacting and nondestructive manner, therefore eliminating the need for electrode attachment [A. Rosencwaig, in *Photoacoustic and Thermal-Wave Phenomena in Semiconductors*, edited by A. Mandelis (Elsevier, New York, 1987); M. Wagner, N. Winkler and H. D. Geiler, Appl. Surf. Sci. 50, 373 (1991); A. Skumanich, D. Fournier, A. C. Boccara and N. M. Amer, Appl. Phys. Lett. 47, 402 (1985); A. Mandelis, A. A. Ward and K. T. Lee, J. Appl. Phys. 66, 5584 (1989); S. J. Sheard and M. G. Somekh, Infrared Phys. 28, 287 (1988)]. A distinct disadvantage of those photothermal techniques, however, is the fact that with either frequency-scanned detection [A. Rosencwaig, in *Photoacoustic and Thermal-Wave Phenomena in Semiconductors*, edited by A. Mandelis (Elsevier, New York, 1987); A. Mandelis, A. A. Ward and K. T. Lee, J. Appl. Phys. 66, 5584 (1989); S. J. Sheard, Ph.D. thesis, University of London, 1987, Chap. 4] or with time-resolved detection [K. Cho and C. C. Davis, IEEE J.

Quantum Electron. QE-25, 1112 (1989)], both free-carrier (plasma) -wave and thermal-wave responses from semiconductors are strongly coupled together. As a result the interpretation of the convoluted experimental data is usually complicated. The task of deconvoluting the two types of responses becomes cumbersome, and this renders much of the analysis qualitative. As an example, the thermoreflectance technique [A. Rosencwaig, in *Photoacoustic and Thermal-Wave Phenomena in Semiconductors*, edited by A. Mandelis (Elsevier, New York, 1987); Chap. 5] produces signals $\Delta R$ which depend on both the ac temperature of the laser-excited semiconductor surface $\Delta T(\omega)$, and on the photogenerated electron-hole plasma wave $\Delta N(\omega)$, $$\Delta R(\omega) = \left(\frac{\partial R}{\partial T}\right)\Delta T(\omega) + \left(\frac{\partial R}{\partial N}\right)\Delta N(\omega). \qquad (6)$$

Very tightly focused ($\sim 1\ \mu m^2$) pump beams can, in principle, lead to the domination of $\Delta R$ by the plasma response, yet this constraint results in the necessity for quite complicated three-dimensional mathematical modelling. Furthermore, it can be detrimental to the study of electronic defects, since the exceedingly high local laser fluences may greatly perturb experiments by saturating trap centers or causing enhanced thermal emission of trapped carriers.

Similarly, pulsed (i.e., impulse response) photothermal radiometry exhibits severe overlap of free-carrier density and thermal effects [K. Cho and C. C. Davis, IEEE J. Quantum Electron. QE-25, 1112 (1989)]. In terms of physical interpretation of signals, the latter technique is considered preferable to the respective frequency-domain (i.e., transfer-function) detection [S. J. Sheard and M. G. Somekh, Infrared Phys. 28, 287 (1988); S. J. Sheard, Ph.D. thesis, University of London, 1987, Chap. 4] due to the inherent ability of transient-response techniques to be interpretable in terms of simple system time-delay constants. The same information can be obtained, in principle, from the frequency-scanned data; however, this method requires the demultiplexing of data over broad frequency ranges, typical of the existing relationship between Fourier transform pairs (i.e., time and frequency domains).

iii) Conventional Electronic Trap and Deep-Level Measurement Methods

The technique of deep level transient spectroscopy (DLTS) has been successfully applied to the study of several types of semiconductors [D. V. Lang, in *Topics in Applied Physics*, edited by P. Braunlich (Springer, New York, 1979), Vol. 37, Chap. 3] and has measured the thermal emission properties of deep levels of impurities and defects [D. V. Lang, J. Appl. Phys. 45, 3023 (1974)]. In its conventional realization DLTS gives a measurement of the thermal electron population lifetime constant of, say, a junction by monitoring the capacitance transient following the application of an electrical pulse across the junction [D. V. Lang, J. Appl. Phys. 45, 3023 (1974)] or optical [D. V. Lang, J. D. Cohen and J. P. Harbison, Phys. Rev. B 25, 5285 (1982); A. Chantre, G. Vincent and D. Bois, Phys. Rev. B 23, 5335 (1981)]. The time constant is determined by comparison with an electronically established "rate window", using a dual-gated boxcar integrator, the gates of which are adjusted through synchronization with respect to the end of the excitation pulse. Thus, for an exponential decay of lifetime $\tau$, such as the carrier recombination in a specific defect level in a semiconductor $$x(t)=e^{-t/\tau}.$$

Once the boxcar gates are fixed and set at times $t_1$ and $t_2$, the output signal can be written $$\Delta S(t)=e^{-t_1/\tau}-e^{-t_2/\tau}$$

with a maximum occurring for a carrier decay time constant, $\tau_{max}$, such that $d(\Delta S)/d\tau = 0$, or $$\tau_{max} = \frac{t_2 - t_1}{\ln(t_2/t_1)}.$$

In DLTS the external parameter which varies the physical decay constant $\tau$ is the equilibrium temperature T of the junction. The inverse of $\tau_{max}$ is the "rate window". Another, less popular method for establishing rate windows is using the lock-in analyzer instead of a boxcar integrator [D. S. Day, M. Y. Tsai, B. G. Streetman and D. V. Lang, J. Appl. Phys. 50, 5093 (1979); J. T. Schott, H. M. Deangelis and W. R. White, Air Force Cambridge Research Laboratories Rap. No. AFCRL-TR-76-0024 (1976); L. C. Kimerling, IEEE Trans. Nucl. Sci. NS-23, 1497 (1976)]. This method is well suited for measuring the frequency content of thermal transients with a superior signal-to-noise ratio (SNR) to conventional transient detection schemes, due to the extremely narrow-band filtering effected by commercially available lock-in analyzers. Deep-level transient spectroscopy is able to characterize imperfections in most semiconducting solids and is widely used in the semiconductor industry. A major disadvantage of this technique is that it is a contacting technique and involves the use of electrodes (or probes) and the measurement of the capacitance transient in p-n junctions, due to levels filled or emptied by injection as they return to equilibrium, as a function of temperature. In actual operation, this capacitance transient is recorded by suitable cyclical repetition of the transient and the data are subject to multichannel signal-averaging. The peaks of the capacitance plot vs. temperature carry information about the energetic location and the concentrations of specific electronic traps in semiconductors.

Apparatus For Measuring Thermal Diffusivity and Electronic Lifetimes

The apparatus for measuring thermal diffusivities and electronic lifetimes of samples using the rate window method according to the present invention and the prior art frequency scan method for purposes of comparison will now be described.

A schematic diagram of the apparatus for measuring thermal diffusivities is shown generally at 10 in FIG. 1. An Ar$^+$ laser 12 (with a wavelength of 488 nm or 514 nm) or any other heating laser with a modulated power up to a few Watts, modulated by an acoustic-optic (A/O) modulator 14 is directed onto the surface of a sample 16 using focusing optics 18. When heating and temperature monitoring is carried out on the same side of the sample, the sample must be thin enough (and of known thickness) such that the front surface temperature is affected by the back boundary. The temperature is monitored in a non-contact manner by measuring the IR radiation emitted from the sample surface. The radiation emitted by the surface of sample 16 is collected and focused onto a detector 22 using off-axis paraboloidal mirrors 24 and 26. The heated area of the surface of sample 16 is centered around the focal point of mirror 24 and detector 22 is at the focal point of mirror 26.

Detector 22 is a liquid-N$_2$ cooled HgCdTe (EG & G Judson model J15D16-M204) with an active area of 1 mm$^2$ and a spectrally sensitive range of 2–10 µm. An AR-coated Ge window 30 with a transmission bandwidth of 2–13 µm is mounted in front of detector 22 to block any visible radiation from pump laser 12. The pump beam spot diameter on sample 16 is ca. 2 mm, which is larger than the maximum profiling depth (<0.5 mm) of interest. This maintains the one-dimensional heat diffusion formalism assumed in the theory. The photothermal signal, which is proportional to the change in the IR radiation emitted from an area viewed by detector 22, is amplified by a pre-amplifier 32 (EG & G Judson model PA-100) before being sent to a digital lock-in amplifier 34 (Stanford Research System, model SR850). Digital lock-in amplifiers exhibit signal-to-noise ratio advantages over analog instruments [see Sect. "Theoretical Proof of SNR Advantage of $\tau_p$-scanned Rate-Window Photothermal Detection"; ii) Quantitative]. Lock-in amplifier 34 is interfaced with a computer 36 so that the frequency scan and the data acquisition and storage are automated. Pulses for the acousto-optic (A/O) modulator to modulate the laser beam intensity pulse profile and frequency/repetition rate (which is also used as the reference signal for the lock-in) are generated by programming the 9513A system Timing Controller output on the Lab Master DMA (Scientific Solutions, Inc.) motherboard. The power density used (at 50% duty cycle) is the same for all the measurements described below. It is necessary to allow the system to come to thermal equilibrium, with the laser on, so that the unmodulated temperature of the sample reaches steady state, before collecting data.

It will be appreciated by those skilled in the art that numerous other configurations for repetitively heating samples and measuring the resulting photothermal signal may be used (e.g. photoacoustic, beam deflection, photopyroelectric). It will also be appreciated by those skilled in the art that rate-window detection can also be accomplished using a narrow pulsewidth pulsed laser and a boxcar integrator to replace the time gated CW laser 12 and/or the lock-in amplifier 34 of FIG. 1. Such an instrument can be the EG & G Model 162, including Model 166 Gated Integrator Module and Model 115 Wideband Preamplifier. Any suitable pulsed laser may also be used (e.g. nitrogen or frequency doubled Nd:Yag with a boxcar integrator. If a boxcar integrator is used, the method of the present invention can be applied without any additional instrumental or computer modifications. The above example is meant to be non limiting and illustrative only.

Frequency Scan Results

Figure 2A:
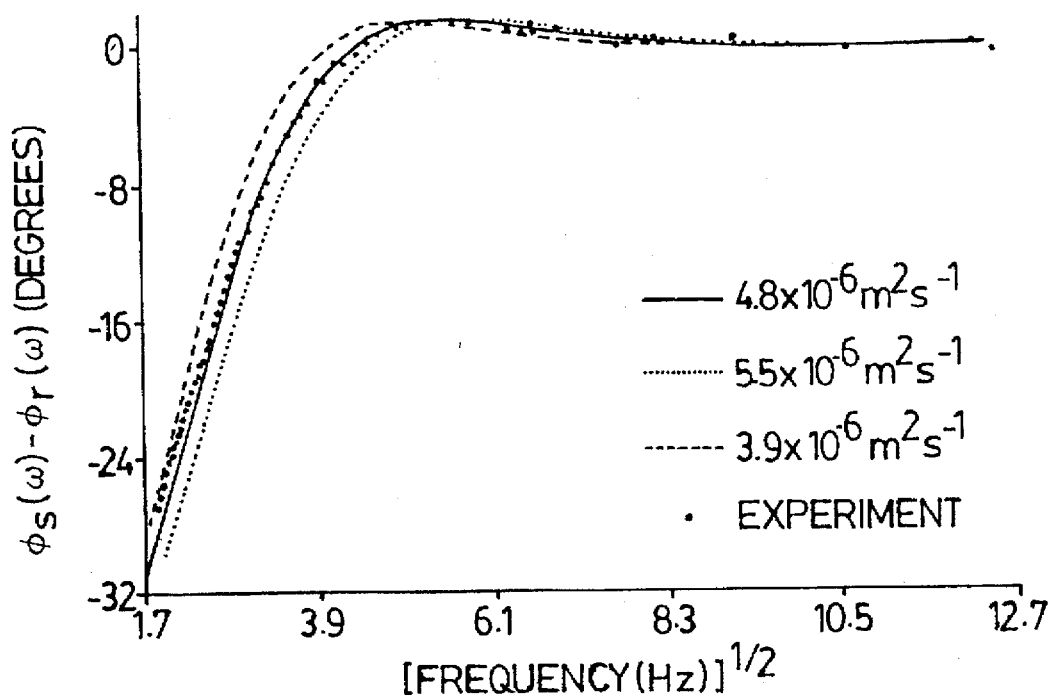
FIG. 2a shows the observed (filled circles) frequency scanned phase data for a 440 μm thick steel plate normalized to a semi-infinite reference sample and the corresponding theoretical curves for thermal diffusivities of $4.8 \times 10^{-6}$ (solid), $5.5 \times 10^{-6}$ (dots) and $3.9 \times 10^{-6}$ (dashes) $m^2 s^{-1}$.
Figure 2B:
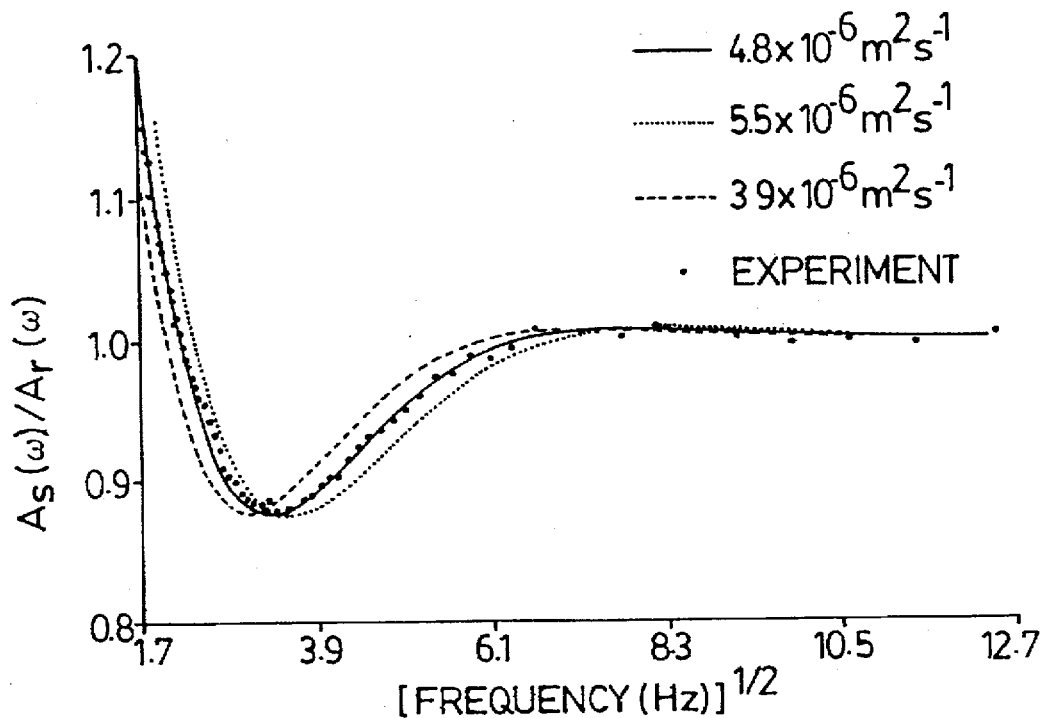
Figure 3A:
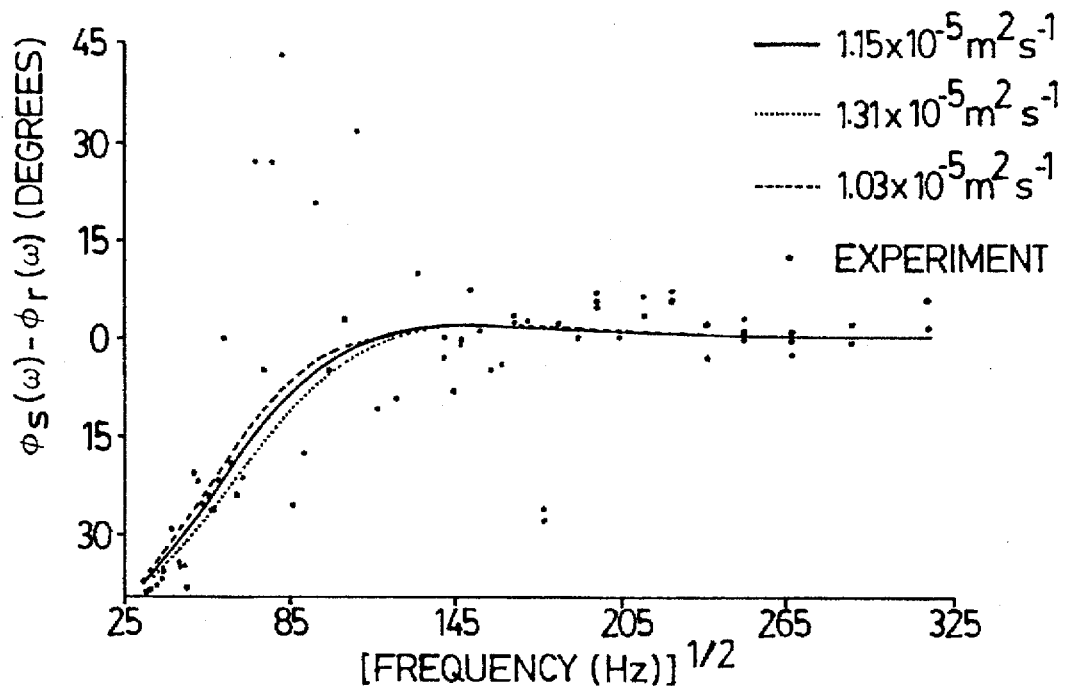
FIG. 3a shows the observed (filled circles) frequency scanned phase data for a 25.4 μm thick metal foil, normalized to a semi-infinite reference sample and the corresponding theoretical curves for thermal diffusivities of $1.15 \times 10^{-5}$ (solid), $1.31 \times 10^{-5}$ (dots) and $1.03 \times 10^{-5}$ (dashes) $m^2 s^{-1}$.
Figure 3B:
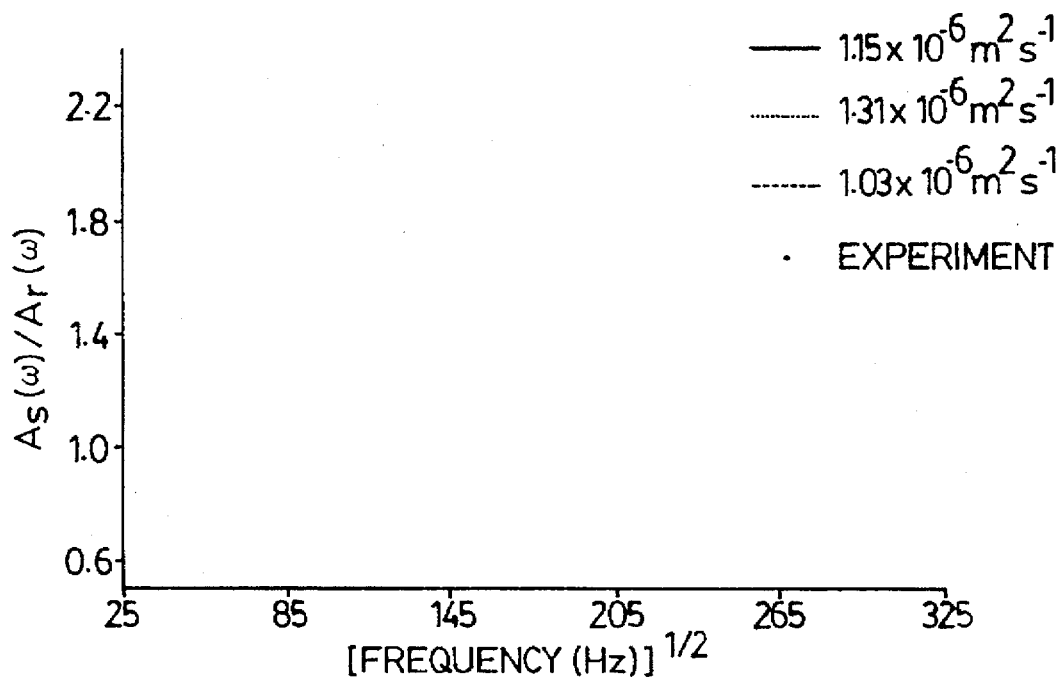

Experimental frequency-scan data (3 Hz to 155 Hz) from a 440 μm thick stainless steel type 304 sample and the corresponding theoretical fit to equation 1 are shown in FIGS. 2a and 2b. The best fit was found to occur for a thermal diffusivity of $4.8 \times 10^{-6}$ m$^2$s$^{-1}$. Two other curves corresponding to $\alpha_s$ of $3.95 \times 10^{-6}$ m$^2$s$^{-1}$ and $5.5 \times 10^{-6}$ m$^2$s$^{-1}$ are also shown in order to assess the sensitivity of the fit to the absolute value of the diffusivity. FIGS. 3a and 3b show similar data from a foil of thickness 25.4 μm from an unknown metallic material within a frequency range of 10–100 kHz. These data exhibit severe scatter around the extremum and are therefore difficult to fit to the theoretical expression, equation 1, with any reasonable degree of accuracy. The theoretical curves correspond to diffusivities of $1.15 \times 10 \times 10^{-5}$, $1.31 \times 10^{-5}$ and $1.03 \times 10^{-5}$ m$^2$s$^{-1}$.

The results in FIGS. 3a and 3b are optimized in the sense that digital lock-in outputs exhibit superior signal-to-noise ratios to conventional analog lock-ins. Yet, the combination of the large scatter observed throughout the measurement frequency range and the relative insensitivity of the theoretical curves to the actual value of $\alpha_s$ for deviations of this parameter up to 40%, and, perhaps, higher, unfortunately leads to the conclusion that frequency-scanned photothermal radiometry is not easily applicable to thin metallic layers.

DETAILED DESCRIPTION OF THE METHODS OF THE PRESENT INVENTION

Rate Window Method of Measuring Thermal Diffusivities and Electronic Lifetimes i) Theoretical Background Of the Rate Window Method The method of measuring thermal diffusivities of the present invention, referred hereinafter as the rate window method (lock-in or boxcar-integrator), involves irradiating a sample with a repetitive square laser pulse of duration $\tau_p$ and period $T_0$. The evolution of the temperature in the sample is governed by the thermal diffusion equation as disclosed in Z. Chen and A. Mandelis, Phys. Rev. B 46, 13 526 (1992) and incorporated herein by reference. Solving this equation in the Laplace domain with appropriate boundary conditions and transforming to the time-domain, one can obtain the temperature evolution, $T_R(t)$, at the irradiated surface given by:

$$T_R(t) = \begin{cases} F_R(t); \ t \leq \tau_p \\ F_R(t) - F_R(t-\tau_p); \ T_0 \geq t \geq \tau_p \end{cases} \quad (7)$$

$$F_R(t) = K\sqrt{t} \sum_{n=0}^{\infty} \left\{ R_{gs}^{2n+1} \ \text{ierfc}\left[\frac{(n+1)L}{\sqrt{\alpha_s t}}\right] + R_{gs}^{2n} \ \text{ierfc}\left[\frac{nL}{\sqrt{\alpha_s t}}\right] \right\} \quad (8)$$

Here K is a constant independent of the characteristic thermal time constant $L^2/\alpha_s$ and the function ierfc(x) is defined as $$\text{ierfc}(x) = \frac{1}{\sqrt{\pi}} e^{-x^2} - x \, \text{erfc}(x) \quad (9)$$

$$\text{erfc}(x) = \frac{2}{\sqrt{\pi}} \int_x^{\infty} e^{-y^2} dy. \quad (10)$$

Since this is a repetitive heating process, it is necessary to take into consideration the effect of earlier pulses. A rigorous calculation which involves solving of the diffusion equation with periodic boundary conditions shows that a simple linear superposition during any pulse interval $$S_R(t) = \begin{cases} F_R(t) + \sum_{k=1}^{\infty} [F_R(t+kT_0) - F_R(t-\tau_p+kT_0)]; \ t \leq \tau_p \\ \sum_{k=0}^{\infty} [F_R(t+kT_0) - F_R(t-\tau_p+kT_0)]; \ T_0 \geq t \geq \tau_p \end{cases} \quad (11)$$

is valid.

In the lock-in rate-window method, $S_R(t)$ is the input to the lock-in amplifier with a reference signal of frequency $1/T_0$. This method has the advantage of combining the superior signal-to-noise ratio of a tuned electronic filter, used in the frequency domain detection, with the simple and straightforward interpretation of the time domain photothermal signal $S_R(t)$. The lock-in measures the fundamental Fourier component of $S_R(t)$ with an amplitude $c_1$ and phase $\phi_1$ given by $$C_1 = (a_1^2 + b_1^2)^{1/2} \quad (12)$$

$$\phi_1 = \tan^{-1}(b_1/a_1)$$

where $$a_1(T_0) = \frac{2}{T_0} \int_0^{T_0} S_R(t)\cos(\omega_0 t)dt, \quad (13)$$

$$b_1(T_0) = \frac{2}{T_0} \int_0^{T_0} S_R(t)\sin(\omega_0 t)dt$$

and $$\omega_0 = \frac{2\pi}{T_0}. \quad (14)$$

Figure 4:
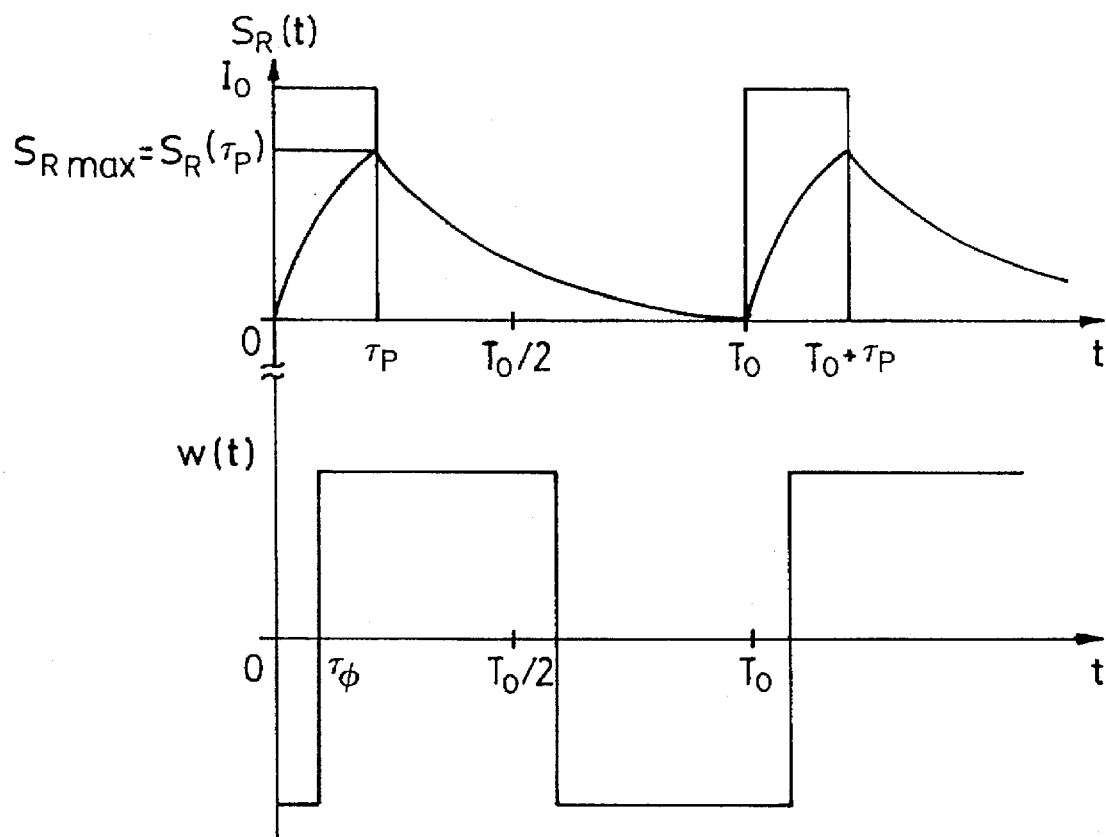
FIG. 4 displays the photothermal repetitive transient signal $S_R(t)$ due to a rectangular pulse of width or duration $\tau_p$ and period $T_0$ with the lock-in amplifier weighting function w(t) shown with the same period and a phase delay $\tau_\phi$.

Now, the in-phase and quadrature components of the lock-in output are obtained by weighting both the corresponding fundamental Fourier components $$f_I(t) = c_1 \cos(\omega_0 t + \phi_1) \quad (15)$$

and $$f_Q(t) = c_1 \sin(\omega_0 t + \phi_1) \quad (16)$$

by the square-wave lock-in reference function w(t) of duration $T_0$. At this point any frequency dependent instrumental phase shifts are taken into consideration by including a time shift $\tau_\phi(T_0)$ into the reference as shown in FIG. 4. The result of this operation under long lock-in filter time constant is $$\begin{aligned} S_I(T_0) &= \frac{1}{T_0} \int_0^{T_0} f_I(t)w(t)dt \quad (17) \\ &= \frac{1}{T_0} \left[ -\int_0^{\tau_\phi(T_0)} f_I(t)dt + \int_{\tau_\phi(T_0)}^{T_0/2 + \tau_\phi(T_0)} f_I(t)dt - \int_{T_0/2 + \tau_\phi(T_0)}^{T_0} f_I(t)dt \right] \\ &= \frac{2c_1}{\pi} \sin[\omega_0 \tau_\phi(T_0) + \phi_1(T_0)] \end{aligned}$$

and similarly $$S_Q(T_0) = -\frac{2c_1}{\pi} \cos[\omega_0 \tau_\phi(T_0) + \phi_1(T_0)]. \quad (18)$$

If the lock-in reference phase is tuned for all $T_0$ so as to align the positive edge of the reference square-wave with the rising edge of the optical pulse, $\tau_\phi(T_0)$ will be zero and the lock-in output signals will be $$S_I(T_0) = \frac{2b_1(T_0)}{\pi} \quad (19)$$

$$S_Q(T_0) = \frac{2a_1(T_0)}{\pi}. \quad (20)$$

Calculations show that the quadrature of the lock-in signal converges (i.e. reaches a particular value which remains unchanged thereafter) after a superposition of about ten pulses in the time domain photothermal signal $S_R(t)$, given by Equation 11 and it agrees with the experimental data, whereas it is computationally very difficult for the in-phase component to converge on the data line. This is probably due to the fact that the cosine weighting function will tend to emphasize the initial part of the decay transient, while the sine weighting function tends to emphasize the later part, see for example C. A. B. Ball and A. B. Conibear, Rev. Sci. Instrum. 62, 2831 (1991). Signal convergence (or saturation) is expected in the form of a "transient steady-state", when dynamic equilibrium is established across a sample with respect to input/output thermal energy balance. This amounts to a stable (constant) baseline for the transient signal, and is established after only a few pulse repetition cycles.

In the photothermal lock-in rate-window method the scanning of the rate window is performed either by changing the period $T_0$ of the repetitive heating pulse with constant pulse duration $\tau_p$, or by changing pulse duration at a fixed period. For measuring thermal diffusivity using fixed period $T_0$ and scanned pulse duration $\tau_p$, forming the present invention, a train of pulses of fixed period $T_0$ at a certain pulse duration $\tau_p$ impinge on the surface of sample 16 for a period of time sufficient to obtain, process and store a photothermal signal. The pulse duration $\tau_p$ is then changed to the next value and the process repeated until the range from between 0 to $T_0$ of $\tau_p$ has been covered.

Cancelling out the instrumental frequency dependence is not straightforward in this technique as in the frequency-scan method. The inventors have observed that most of the instrumental effects come from the frequency dependent phase of the lock-in amplifier, especially below 30 Hz and above 10 kHz (models SR850 and EG & G Model 5210). In the case of rate-window $T_0$ scan, it is possible to find the function, $\tau_\phi(T_0)$, from a polynomial fit to a frequency-scan phase data from a homogeneous semi-infinite reference sample. These phase data can be stored in the computer memory and used for all subsequent rate-window scans involving the same instrumental set-up. In the case of pulse duration scan, the lock-in phase can be tuned manually so that the phase of the signal from a homogeneous semi-infinite reference sample at frequency $1/T_0$ (50% duty cycle) is $-45°$ as expected theoretically from Equation 1 in the limit $L \to \infty$ (i.e. Equation 5), before taking rate-window data. This makes scanning the pulse duration more convenient because there is no change in the instrumental transfer function, which only depends on the $T_0$. Nevertheless, this method has a resolution disadvantage with regard to the position of the quadrature extremum, as will be seen below.

In the photothermal boxcar-integrator rate-window method the same approach can be used: The boxcar time gates can be set at a fixed ratio of the repetition period $T_o$ and either $T_o$ or $\tau_p$ can be subsequently scanned, producing an extremum in the photothermal signal response. According to a theoretical comparison of the lock-in and boxcar rate-window signal-to-noise ratios, disclosed by Z. Chen and A. Mandelis, Phys. Rev. B 46, 13526 (1992-II), the SNR of the boxcar detection is always lower than that of the lock-in detection (for the important case of exponential time decays). The boxcar SNR approaches monotonically that of the lock-in detection, as the gate width of the boxcar increases towards $T_o/2$.

Therefore, in the remainder of the description of the invention, and by way of optimum example, rate-window scans are specified to be lock-in rate-window scans. The invention, however, is understood to include boxcar rate-window scans, with fixed gate separation relationship and scanned $\tau_p$; or impulse-response scans using a pulsed laser source and time-scanned boxcar gates with fixed separation relationship to each other.

The method of measuring electronic recombination lifetimes of semiconductors of the present invention involves exactly the same instrumental and experimental arrangement as for the thermal diffusivity rate-window method. Instead of Eq. (7), however, electronic diffusion in a semiconductor, following laser optical excitation of free carriers, results in the following expression as derived in Z. H. Chen, R. Bleiss, A. Mandelis, A. Buczkowski and F.

Shimura, J. Appl. Phys. 73, 5043 (1993) and incorporated herein by reference:

$$S_{IR} = \begin{cases} F_{IR}(t; \tau, \tau_a, \tau_s); & t \leq \tau_p \\ F_{IR}(t; \tau, \tau_a, \tau_s) - F_{IR}(t - \tau_p; \tau, \tau_a, \tau_s); & t \geq \tau_p \end{cases} \quad (21)$$

where $$F_{IR}(t; \tau, \tau_a, \tau_s) = C\zeta \frac{\eta I_0}{hv} \frac{1}{\sqrt{\tau_s} - \sqrt{\tau_a}} \left\{ \frac{\sqrt{\tau_s}}{\tau_s^{-1} - \tau^{-1}} \left[ \sqrt{\frac{\tau}{\tau_s}} \, erf\left(\sqrt{\frac{t}{\tau}}\right) + e^{-t/\tau} W\left(\sqrt{\frac{t}{\tau_s}} - 1\right) \right] - \frac{\sqrt{\tau_a}}{\tau_a^{-1} - \tau^{-1}} \left[ \sqrt{\frac{\tau}{\tau_a}} \, erf\left(\sqrt{\frac{t}{\tau}}\right) + e^{-t/\tau} W\left(\sqrt{\frac{t}{\tau_a}}\right) - 1 \right] \right\}. \quad (22)$$

Here $\zeta$ is a constant related to the infrared radiation detector, and C is a constant independent of any photoexcited carrier characteristic time constants, i.e., Eqs. (23)–(24) below.

$$\tau_a = \frac{1}{a^2 D} \quad (23)$$

is the time required for a carrier to diffuse a depth equal to the optical absorption length, 1/a. Similarly, $$\tau_s = \frac{D}{s_1^2} \quad (24)$$

is a time constant due to recombination at surface defects, which is dependent on surface recombination velocity and carrier diffusion coefficient.

$$W(z) = e^{z^2} erfc(z) \quad (25)$$

is a function encountered in time-domain diffusion-type problems, where erfc(z) is the complementary error function defined by Eq. (10).

For opaque semiconductors in which $\tau_a \ll \tau$, and $\tau_a \ll \tau_s$, Eq. (22) can be simplified to $$F_{IR}(t; \tau, \tau_s) = C\zeta \frac{\eta I_0}{hv} \frac{1}{\tau_s^{-1} - \tau^{-1}} \left[ \sqrt{\frac{\tau}{\tau_s}} \, erf\left(\sqrt{\frac{t}{\tau}}\right) + e^{-t/\tau} W\left(\sqrt{\frac{t}{\tau_s}}\right) - 1 \right]. \quad (26)$$

In the special case of very low surface recombination velocity ($s_1 \rightarrow 0$, i.e., $\tau_s \gg \tau$), Eq. (26) can be further simplified, as shown in Eq. (27).

It is evident from Eq. (27) that the infrared radiometric signal is a pure exponential function dependent on the bulk lifetime $\tau$ only, when the carrier surface recombination $$F_{IR}(t; \tau) = C\zeta \frac{\eta I_0}{hv} \tau(1 - e^{-t/\tau}) \quad (27)$$

velocity is very low. In what follows, we will concentrate on the discussion of this case, which implies high quality material surfaces, such as those present in the inventors' experiments. In the case where $s_1$ is not negligible, simulations of the full Eq. (22) and other theoretical and experimental results show that a single exponential cannot describe the early time-decay of the free photoexcited carrier density. That decay profile is faster than the exponential. Therefore, in the analysis purely exponential decay has been used as the unambiguous criterion for the photothermal (PTR) signal domination by a bulk type of carrier recombination mechanism alone.

Figure 5:
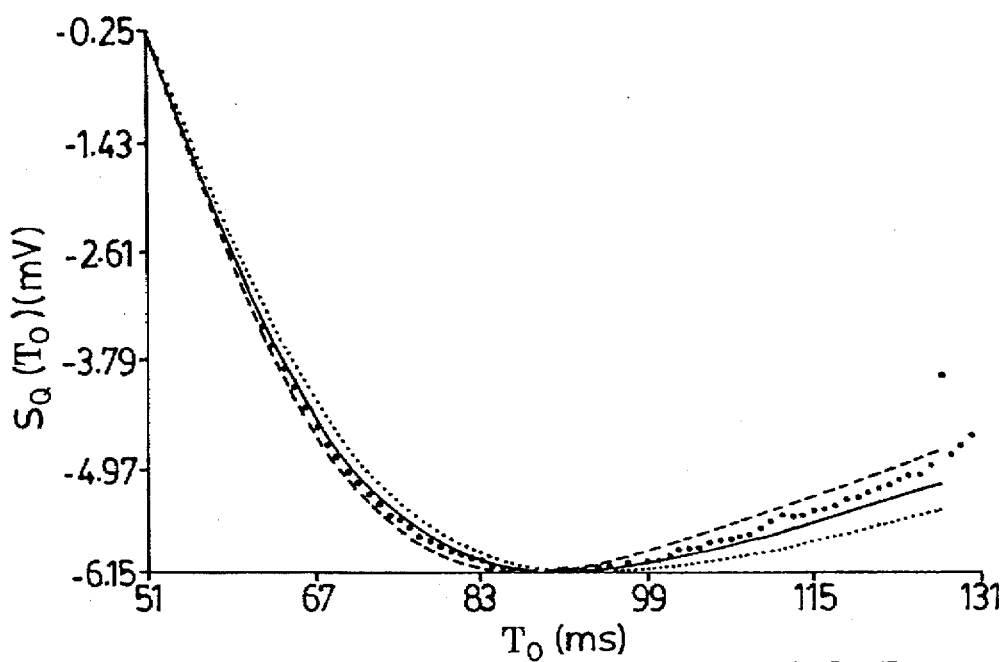
FIG. 5 displays the observed quadrature data (filled circles) from a rate-window $T_0$-scan for the 440 μm steel plate of FIGS. 2a and 2b and the theoretical curves (normalized to the experimental minimum) corresponding to diffusivities of $4.8 \times 10^{-6}$ (solid), $5.5 \times 10^{-6}$ (dots) and $3.9 \times 10^{-6}$ (dashes) $m^2 s^{31\ 1}$.
Figure 6:
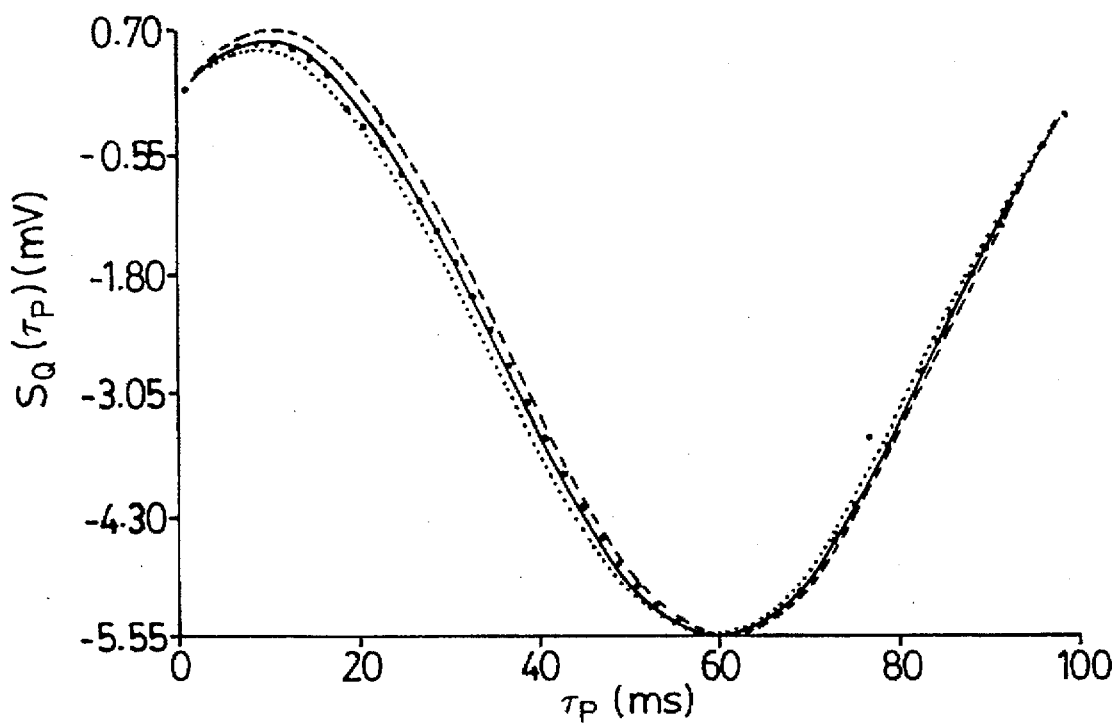
FIG. 6 displays the observed quadrature data (filled circles) from a rate-window $\tau_p$-scan for the 440μm steel plate of FIGS. 2a and 2b and the theoretical curves (normalized to the experimental minimum) corresponding to diffusivities of $4.8 \times 10^{-6}$ (solid), $5.5 \times 10^{-6}$ (dots) and $3.9 \times 10^{-6}$ (dashes) $m^2 s^{31\ 1}$.

The method may be carried out with both a boxcar integrator or a lock-in amplifier. For the lock-in rate window method gives distinct advantages over the boxcar rate-window method since analysis shows in the former case that in the case of extrenum the model gives numerically $(T_0)_{max} = 2.5681\tau + 1.9973\tau_p$ as derived in derived in Z. H. Chen, R. Bleiss, A. Mandelis, A. Buczkowski and F. Shimura, J. Appl. Phys. 73, 5043 (1993) and incorporated herein by reference. Therefore, when scanning the repitition period of the laser pulse ($T_0 > \tau_p$), the period $(T_0)_{max}$ at which a rate-window signal maximum occurs is very simply determined by the carrier bulk lifetime $\tau$ and the pulse duration $\tau_p$ only, provided that the surface recombination lifetime is long and therefore not recombination rate-limiting.

ii) Rate Window Scan Results a) Variable $\tau_p$, Fixed $T_0$, To Measure Thermal Diffusivity of Metal Foils Experimental quadrature signal data from a rate-window scan by scanning the period from 51 ms to 130 ms with a pulse duration of 50 ms, and the corresponding theoretical fit $S_Q(T_0)$ for the same stainless steel sample described earlier are shown in FIG. 5. The three theoretical curves correspond to the same thermal diffusivities used to calculate frequency scan data in FIG. 2 and the best fit is entirely consistent with the frequency scan data. These data were taken with the lock-in phase tuned to a semi-infinite reference sample at 100 ms (10 Hz), which is the 50% duty cycle point. The minimum occurs around that point, and the theoretical curves were calculated using Equation 19. The discrepancy between the data and the theory at longer periods may be due to the lack of adequate compensation for the instrumental effects. It is interesting to note that an analogous divergence of the frequency-scanned phase data from the theoretical fit on FIG. 2a is also evident in the low-frequency regime of that Figure. The quality (SNR) of this rate-window data and the resolution of the extremum are comparable to the frequency-scan data of FIG. 1. FIG. 6 shows the experimental quadrature data from a rate-window scan at a fixed period of 100 ms and a variable pulse duration (1 ms-99 ms) for the same sample. Again, the best fit corresponds to a diffusivity of $4.8 \times 10^{-6}$ m$^2$s$^{-1}$, but no discrepancies between data and theory are evident anywhere in the scanned time range. Here, the reference phase was adjusted at 10 Hz (100 ms, which is the scan period used) such that the signal phase from a semi-infinite reference sample was $-45°$ and was valid for all the data points providing an excellent fit. Unfortunately, the sensitivity of the position of the second extremum (minimum) to the variations in the diffusivity is extremely poor. Therefore, it was found necessary to fit the whole curve.

Figure 7:
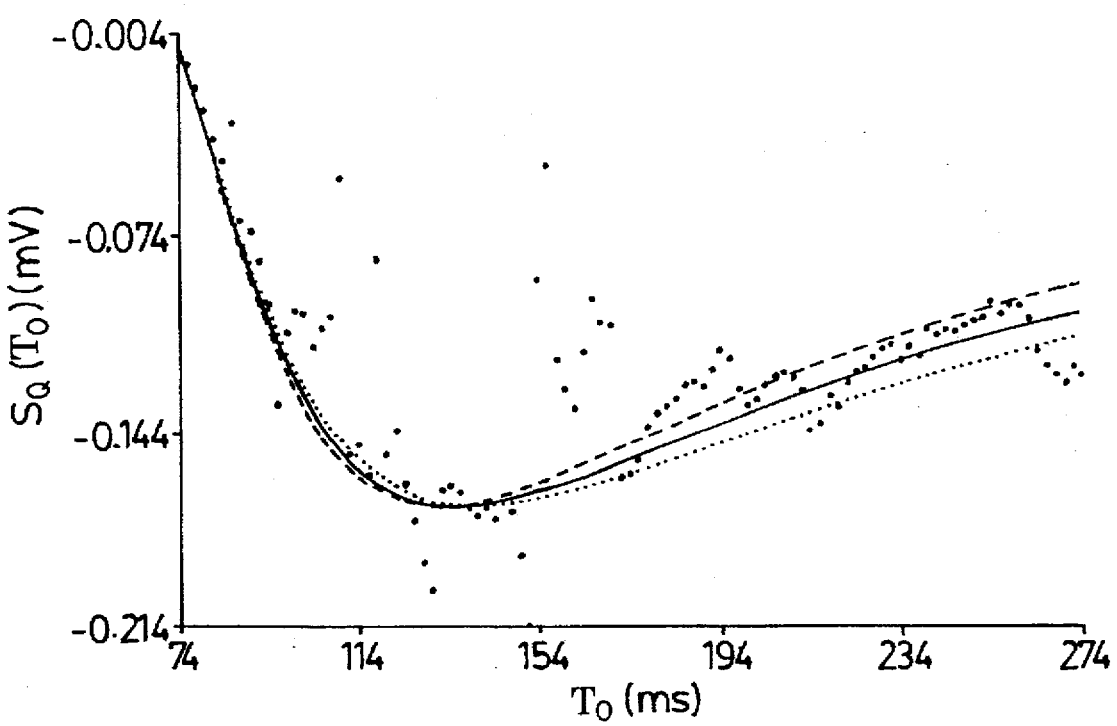
FIG. 7 displays the observed quadrature data (filled circles) from a rate-window $T_0$-scan for the 25.4 μm thick metal foil of FIGS. 3a and 3b and the theoretical curves (normalized to the experimental minimum) corresponding to diffusivities of $1.15 \times 10^5$ (solid), $1.31 \times 10^{-5}$ (dots) and $1.03 \times 10^{-5}$ (dashes) $m^2 s^{-1}$.

Rate-window scan data at a fixed pulse duration of 731 µs from the metal foil of thickness 25.4 µm described earlier are shown in FIG. 7. The lock-in phase was adjusted at 6.849 kHz (146 µs), which is the 50% duty cycle point. The instrumental frequency dependence of the phase was relatively flat in the frequency range of these data. The range of diffusivities ($1.31 \times 10^{-5} - 1.03 \times 10^{-5}$ m²s⁻¹) that could be reasonably fitted, with a median value (solid line) of $1.15 \times 10^{-5}$ m²s⁻¹ is also shown in FIG. 7. Note that the same values were used to calculate the theoretical curves in FIG. 3, however, it is clear that the possible range of diffusivities for the frequency-scan data is much wider owing to their poorer SNR, the absence of pronounced extrema in both amplitude and phase data, and the wide disagreement between normalized amplitude data and the theoretical curves around the minimum of FIG. 3b. The corresponding rate-window pulse duration scan at a fixed period of 146 µs is shown on FIG. 8. This clearly shows a much better signal-to-noise ratio than either FIG. 7 or FIG. 3, with the tolerance in the acceptable $\alpha_s$ values being less than 13%.

The method of dynamically measuring thermal diffusivities using scanned pulse duration, fixed period disclosed herein has been compared with techniques using fixed pulse duration, variable period and conventional frequency scanning methods. Results obtained with two non-limiting sample thicknesses have been presented, one with long thermal transport time $L^2/\alpha_s$ where low frequency measurements are required and another sample with short thermal transport time where high frequency measurements are required. For high frequency measurements, due to the drop in the photothermal signal amplitude, there is a considerable decrease in the signal-to-noise ratio for a given laser irradiance.

Figure 8:
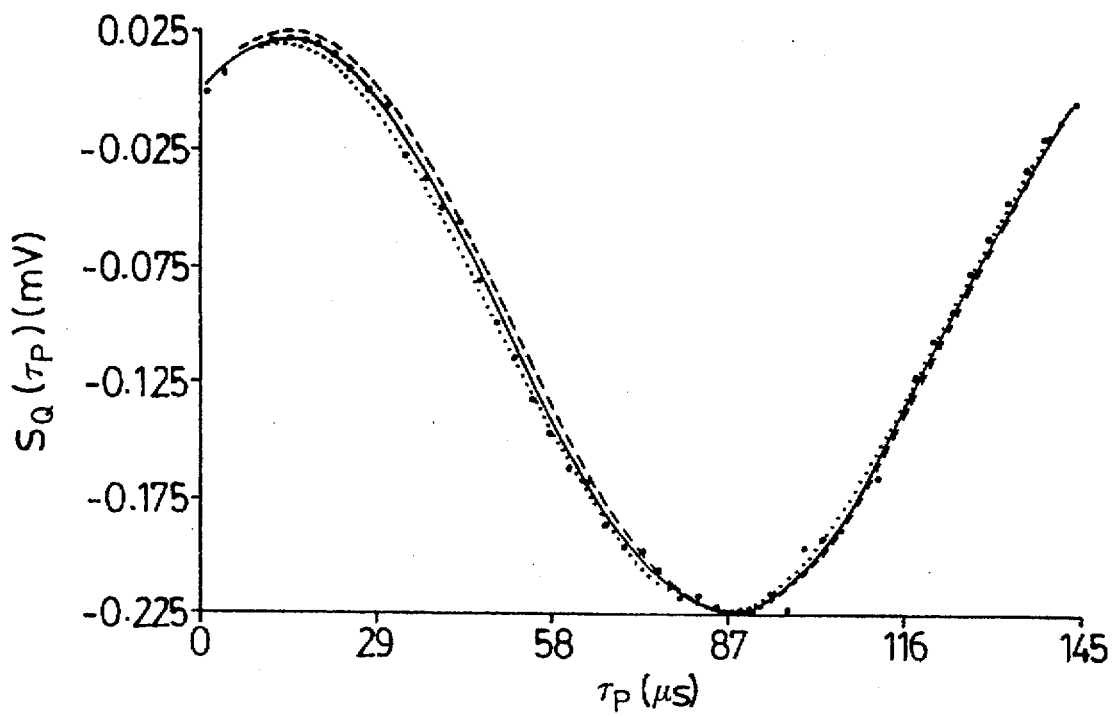
FIG. 8 displays the observed quadrature data (filled circles) from a rate-window $\tau_p$-scan for the 25.4 μm thick metal foil of FIGS. 3a and 3b and the theoretical curves (normalized to the experimental minimum) corresponding to diffusivities of $1.15 \times 10^5$ (solid), $1.31 \times 10^{-5}$ (dots) and $1.03 \times 10^{-5}$ (dashes) $m^2 s^{-1}$.

At high frequencies, the pulse-duration scanned lock-in rate-window method gives signal-to-noise ratios superior to both frequency-scanned detection and repetition period-scanned rate-window detection, as seen from FIGS. 3, 7 and 8. This rate-window technique requires a theoretical fit to the data over a significant range of pulse durations (approx. ±0.2 $T_0$ on either side of the extremum) to determine the best-fit value of the thermal diffusivity, owing to the lack of positional resolution of the curve extrema. Excellent fits are possible resulting in $\alpha_s$ value determinations in thermally thin samples much better than the uncertainty limits of ±13% shown in FIG. 8. By comparison, using the same instrumentation and thin foil sample, the repetition period-scanned rate-window technique gave the value of $\alpha_s$ with uncertainty in the range of ±13%, FIG. 7, due to the degraded SNR. Here, a theoretical fit to the entire $T_0$-scanned range is necessary, while its potential advantage of higher minimum positional resolution than a $\tau_p$ scan is of little relevance because of the increased noise. In addition, the instrumental transfer function can be cancelled out conveniently in the $\tau_p$ scan, and this is not the case with $T_0$-scanned rate-window detection. Finally, the conventional frequency-scanned method is by far the worst, exhibiting extremely degraded SNR resulting in unacceptable high uncertainties in the measurement of $\alpha_s$ values. In fact, the theoretical curves in FIG. 3 corresponding to thin metal foil diffusivity values of $1.03-1.31 \times 10^{-5}$ m²s⁻¹ were drawn after the best-fit value was estimated in FIG. 8. Otherwise, there would be no possible estimate of the most probable $\alpha_s$ value in the presence of the high noise levels of FIG. 3.

Figure 9:
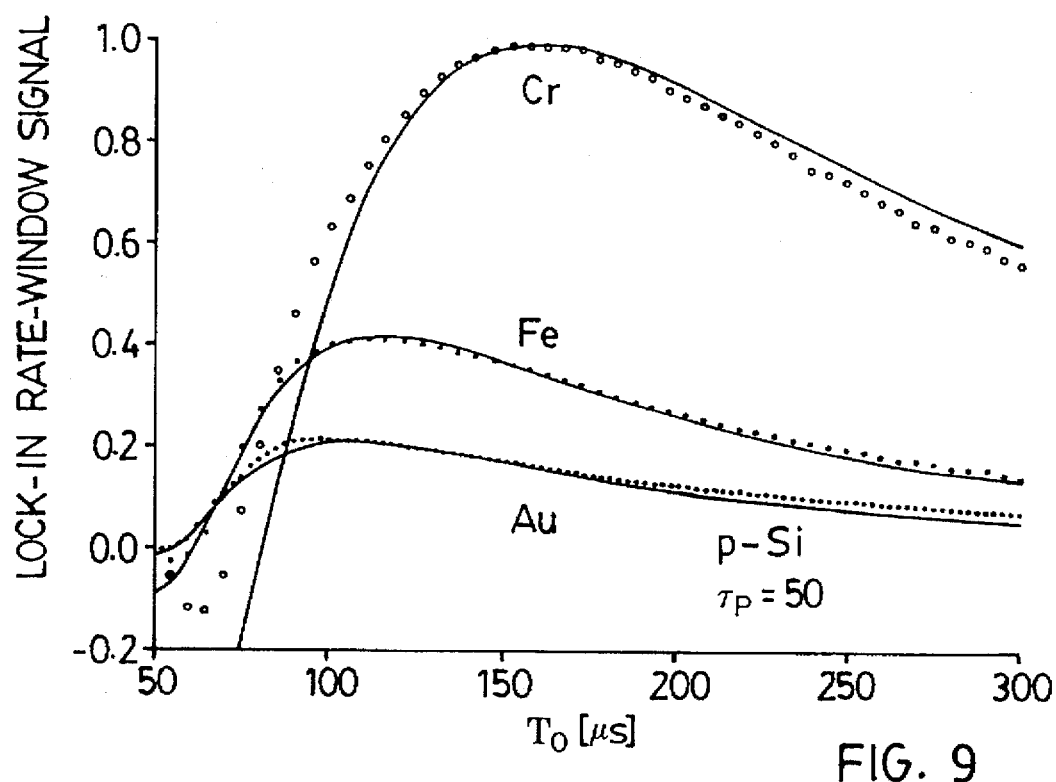
FIG. 9 is the lock-in photothermal radiometric rate window signals of Cr-, Fe-, and Au-doped p-Si wafers with pulse duration $\tau_p$=50 μs and where the solid lines are theoretical simulations.

A further advantage of the scanned pulse duration $\tau_p$ method of measuring thermal diffusivities disclosed herein is that phenomena occurring on time scales $\geq 1$ µs can be monitored by scanning $\tau_p$, while using an instrument that can only "see" at most $10^5$ Hz or $\geq 10$ µs.

b) Variable $T_0$, Fixed $\tau_p$ To Measure Photoexcited Carrier Lifetimes and Thermal Diffusivity of Semiconductors The lock-in photothermal rate-window in-phase signals of Cr-, Fe-, Au-doped p-type Si wafers are shown in FIG. 9. This Figure shows the excellent resolution of the lock-in rate-window detection technique, concerning the determination of the values of the photoexcited carrier bulk recombination lifetime from the curve maxima. The superior S/N ratio lock-in rate-window determination of the maximum in the fundamental Fourier component of the photothermal transient has a $\tau$ resolution of 1 µs, limited only by the dynamic range of the data acquisition system. An order of magnitude improvement is expected with an extended dynamic range system timing controller.

In FIG. 10 the inventors applied the lock-in Rate-Window Photothermal Radiometry (RW-PTR) to Cr-doped n-type Si, with preoxidized and etched high-quality surface, a sample which exhibits strongly overlapping carrier recombination and thermal conduction transient behaviour. By choosing appropriate pulse durations (i.e., acousto-optically time gating a cw laser beam) for the first time they have been able to separate the two transient contributions completely and measure the respective time-delay constants with superior resolution to both frequency- and time-domain conventional methodologies. This ability of RW PTR enormously simplifies the analytical complexity of conventional photothermal-based semiconductor diagnostic techniques, such as thermoreflectance [A. Rosencwaig, in *Photoacoustic and Thermal-Wave Phenomena in Semiconductors*, edited by A. Mandelis (Elsevier, New York, 1987), Chap. 5] and frequency-domain PTR [S. J. Sheard and M. G. Somekh, *Infrared Phys.* 28, 287 (1988)]. Two experimental runs were performed at each wavelength, one with $\tau_p = 30$ µs and a second run with $\tau_p = 1$ ms. The temperature rises were estimated to be less than 1K. in both cases.

Figure 10A:
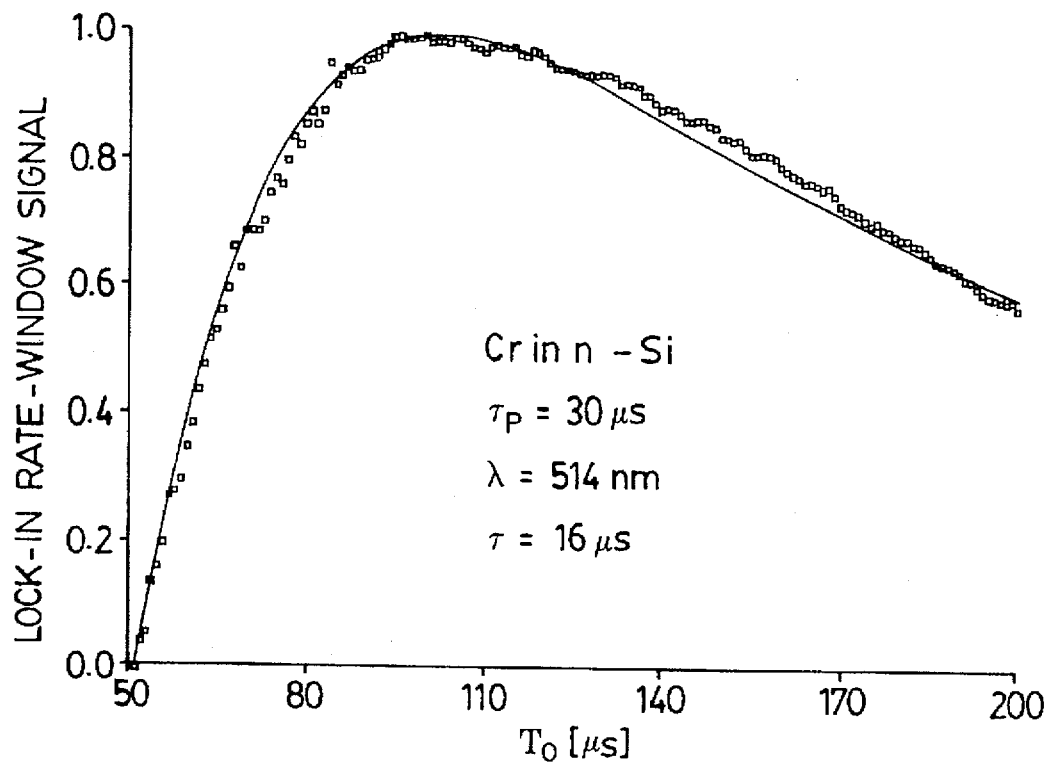
FIG. 10a is the same measurement as FIG. 9 using a Cr-doped n-Si wafer and a repetitive square laser pulse of duration $\tau_p$=30 μs at 514 nm photon excitation, where the solid lines are theoretical simulations.
Figure 10B:
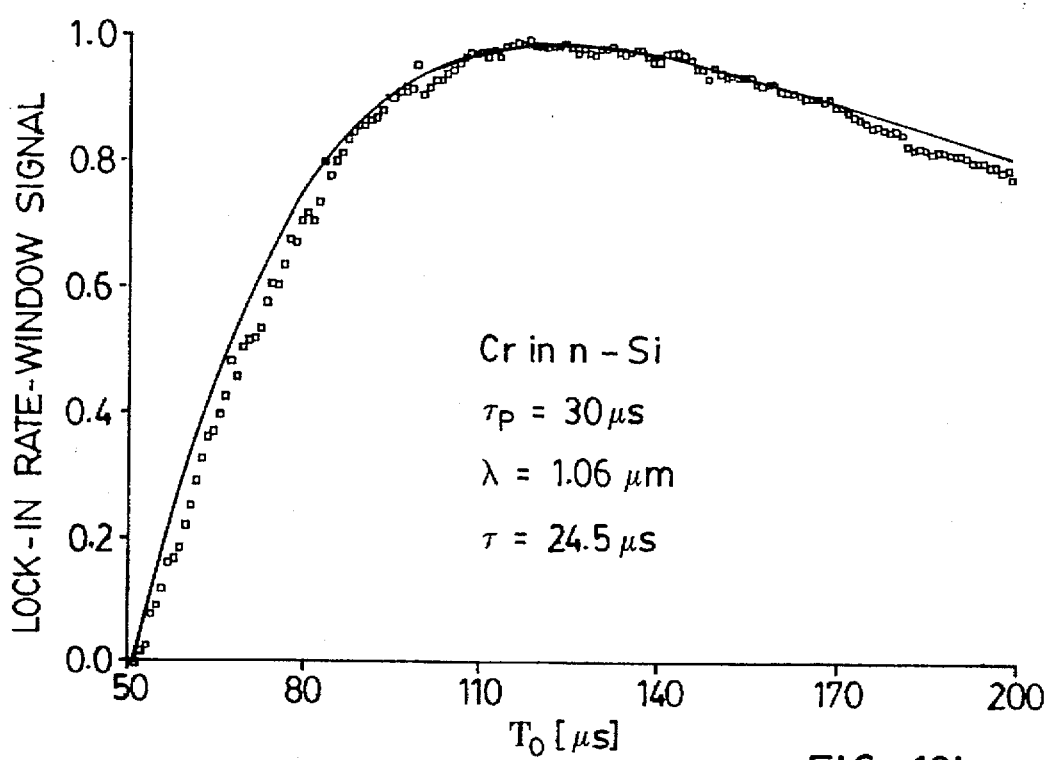
FIG. 10b is the same measurement as FIG. 9 using a Cr-doped n-Si wafer and a repetitive square laser pulse of duration $\tau_p$=30 μs at 1.06 μm photon excitation, where the solid lines are theoretical simulations.

FIGS. 10a and 10b show the lock-in RW-PTR in-phase signal as a function of the laser time-gated square pulse repetition period $T_0$, resulting from a pulse of duration $\tau_p = 30$ µs. The solid lines are the theoretical simulations using the expression for the fundamental Fourier component $b_1$ of the repetitive transient PTR signal $S_{IR}(t;\tau)$ over the period $T_0$, using the fact that the measured fast transient decay was a purely exponential function:

$$S_{IR}(t;\tau) = C_1 \tau \begin{cases} 1 - e^{-t/\tau}, & t \leq \tau_p \\ (e^{\tau_p/\tau} - 1) e^{-t/\tau}, & t \geq \tau_p \end{cases} \quad (28)$$

and $$b_1(\tau;T_0) = C_2 \tau \left( 1 - \cos(\omega_0 \tau_p) + \frac{\omega_0}{\sqrt{\tau^{-2} + \omega_0^2}} [\sin(\omega_0 \tau_p + \theta) - (1 + e^{-T_0 - \tau_p)/\tau} - e^{-T_0/\tau}) \sin\theta] \right), \quad (29)$$

where $$\theta = \tan^{-1}(\omega_0 \tau), \quad \omega_0 = 2\pi/T_0, \quad (30)$$

$C_1$ and $C_2$ are constants independent of any photoexcited carrier characteristic time constants, and $\tau$ is the carrier bulk recombination lifetime.

The difference in lifetime $\tau$ between the results obtained with the Ar and Nd-YAG laser, FIGS. 10(a) and 10(b) respectively, can be explained by the widely different optical penetration depths of the two excitation pulses. The 514 nm pulse probes a region very close to the surface, in which near-surface defects can provide an additional free-carrier recombination channel, thus shortening the effective lifetime. On the other hand, the deeply penetrating 1.06 μm pulse is expected to give a better measurement of the true value of the bulk recombination lifetime. In this case near-surface recombination is much less significant in its contribution to the effective lifetime, and therefore the effective lifetime is longer and characteristic of bulk processes.

Figure 10C:
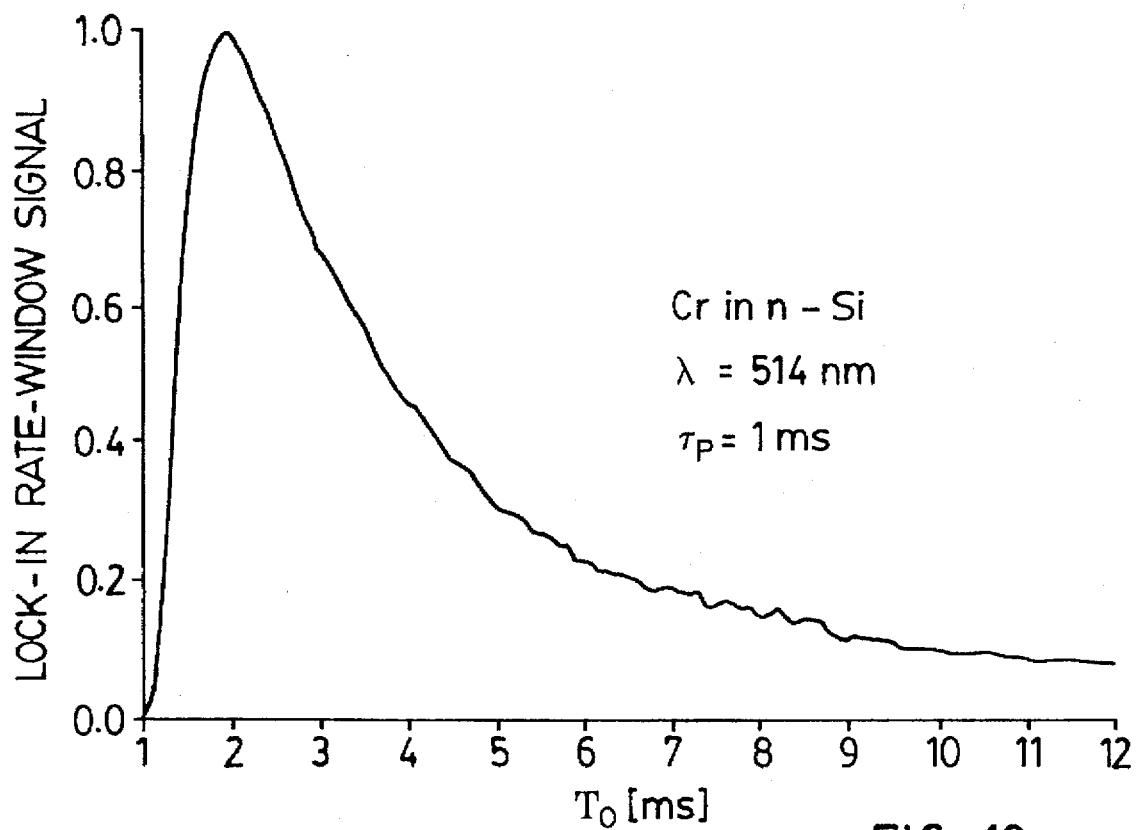
FIG. 10c is the same measurement as FIG. 9 using a Cr-doped n-Si wafer and a repetitive square laser pulse of duration $\tau_p$=1 ms (thermal) at 514 nm photon excitation.

When the pulse duration was increased to $\tau_p=1$ ms, the lock-in RW-PTR response of the Cr-doped silicon wafer to the Ar$^+$ laser excitation is shown in FIG. 10(c). This response, too, is normalized to unity for convenience. A very similar curve was obtained with Nd:YAG laser excitation. The maximum of the in-phase signal at about 2 ms from the onset of the pulse is in good agreement with domination of the infrared radiometric signal by a thermal transient, which in the 500-μm thick free-standing Si wafer requires a round-trip time [Z. H. Chen and A. Mandelis, Phys. Rev. B 46, 13526 (1992)]

$$t_r = L^2 \pi/4 a_s = 1.96 \text{ ms}. \quad (31)$$

Comparing FIGS. 10a and 10b with FIG. 10c shows the ability of RW photothermal detection to completely separate out electronic and thermal transport contributions to overlapping PTR signals from a Cr-doped Si wafer. This can be done with excellent temporal resolution, by a simple change in $\tau_p$ and judicious choice of the $T_o$ scale. The inventors have obtained similar results with Fe-doped Si wafers also. Those skilled in the art will appreciate that the highly resolved results shown in FIGS. 10a, 10b and 10c cannot be obtained either with frequency-scanned PTR detection, because of the multiplexed nature of this methodology, or with pulsed laser excitation, due to the fixed (i.e. noncontinuously variable over wide frequency ranges) repetition rate and pulse duration of current laser technologies.

iii) Photothermal Deep-Level Transient Spectroscopy (PTR-DLTS)

Photothermal Radiometric Deep Level Transient Spectroscopy (PTR-DLTS) is a non-contact DLTS measurement which detects the blackbody radiation by the energy release due to charge carrier recombination in semiconductors over a wide range of temperatures.

Figure 11:
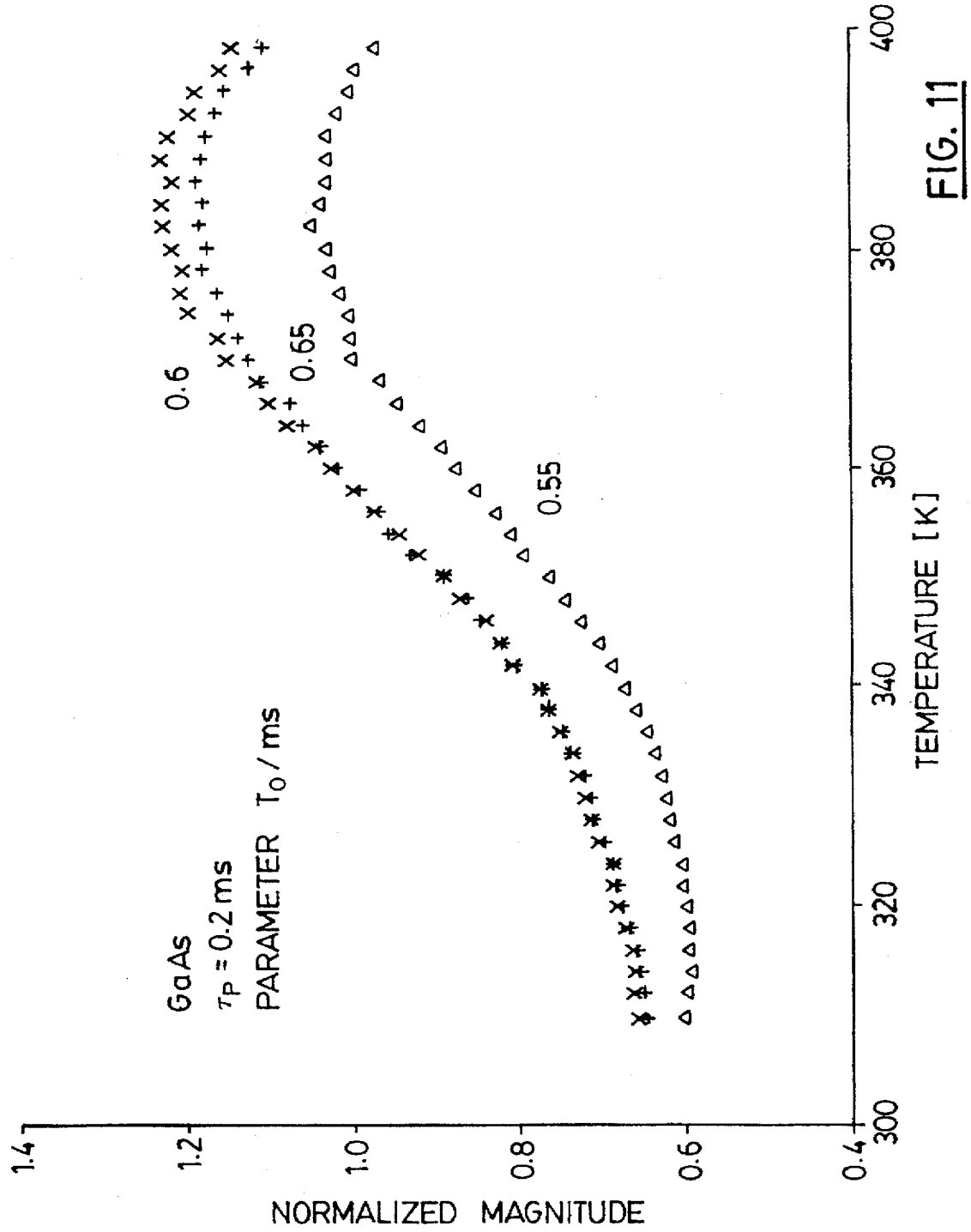
FIG. 11 is a photothermal deep-level transient spectrum of the EL2 electronic level in semi-insulating GaAs using a repetitive square laser pulse of duration $\tau_p$=0.2 ms wherein the three spectra correspond to pulse repetition periods 0.55, 0.6 and 0.65 ms as labelled.

To carry out a PTR-DLTS measurement, the semiconductor sample is placed on a heater/cooler. This heater/cooler has to be capable of the usual temperature range for DLTS measurements. It can be mounted on a movable stage to allow mapping. The rest of the necessary instrumentation is identical to the embodiment of the apparatus of FIG. 1. The spot-size of a switchable laser beam and infrared collection optics are both adjusted to the same point of the sample. The laser beam is switched on for a certain pulse duration and causes the excitation of the charge carrier system. After switching off the laser a recombination process takes place. The released recombination energy causes a temporary peak in the temperature and therefore in the radiation signal of the sample. After every time period this process is repeated. The IR detector is connected with a lock-in amplifier. By heating/cooling the sample one gets a radiation signal related to the excitation pulse parameters over the temperature range of the heater/cooler. The result of the measurement is a set of curves which show the excitation related variation of the photothermal radiometric signal in dependence on the temperature for several (fixed) pulse parameters. The magnitude of the photothermal signal S measured with the lock-in amplifier depends on the temperature change $\Delta T$ due to relaxation processes and on the mean temperature:

$$S \propto \sigma T_B^3 \Delta T \quad (32)$$

where $T_B$ is the background (heater) temperature. The correction by $\sigma T_B^3$ leads to a set of curves which are proportional to the temperature change and therefore to the energy released by the charge carrier recombination. These curves usually have one or more extrema. These extrema are correlated to energy levels that are involved in the carrier injection or trapping process. The variation of the time period or the frequency leads to a variation of the temperature at which the extrema appear. In the case of a single level recombination an Arrhenius plot of the time periods in dependence on the temperatures of the extrema may lead to a value for the energy level. FIG. 11 shows three PTR-DLTS spectra from a Semi-Insulating GaAs wafer, with the peak at approx. 380K. characteristic of the EL2 level in this material [G. M. Martin et al., J. Phys. C: Solid St. Phys. 13, 3855 (1980)].

Theoretical Proof of SNR Advantage of $\tau_p$-scanned Rate-Window Photothermal Detection i) Qualitative In agreement with detailed theoretical considerations of the SNR advantage of the $\tau_p$- or $T_o$-scanned rate-window method over the frequency-scanned approach (see below), it is clear that the transient nature of the rate-window signal is responsible for it. Qualitatively, the lock-in amplifier captures the first Fourier coefficient of the photothermal transient in the former case; in the latter case it monitors the fundamental Fourier coefficient of the harmonic photothermal signal. It is well known from time- and frequency-domain analyses of photothermal signals that in the thermal transient the optically imparted energy distributes itself in such a manner that it provides the strongest response at times immediately following the pulse cutoff, see A. Mandelis, in *Topics in Current Physics*, Vol. 47, edited by P. Hess, (Springer-Verlag, Heidelberg, 1990) Chap. 8. This is precisely the range of scanned times involved in the rate-window technique which therefore yields a strong fundamental coefficient magnitude of the Fourier series representation of the repetitive pulse. Conversely, in harmonic photothermal analysis the fundamental Fourier coefficient of the repetitive 50% duty cycle pulse decreases in magnitude in inverse proportion to the strength of the first Fourier coefficient of the time-domain pulse, due to the inverse relationship between time- and frequency-domain and the Parseval theorem, see B. P. Lathi, *Communication Systems*, (J. Wiley & Sons, Inc., New York, 1968) Chap. 2.7.

Therefore, fast photothermal phenomena are expected to yield fundamental Fourier coefficients of superior strength in the transient repetitive pulse mode to the one allotted to the respective high frequency fundamental component under harmonic excitation, and the higher the frequency, the higher the strength contrast of the fundamentals in the two transform domains. The result is a higher SNR for the transient response.

ii) Quantitative a. Lock-in Amplifier Output Signal

An input time-dependent (non-stationary) signal F(t) to a digital lock-in amplifier (LIA) in the presence of noise n(t) is multiplied with a reference waveform $e_R(t;\omega_o)$ and introduced into the low-pass filter of transfer function H(ω). In the case of a two phase/vector LIA there exists a second channel, the reference phase of which is shifted by 90° with respect to $e_R(t;\omega_o)$. The output of the mixer of this stage is introduced to an identical low-pass filter H(ω). The two outputs constitute the in-phase (IP) and quadrature (Q) components of the LIA signal, respectively. All lock-in detection schemes can be decomposed into the basic system structure shown in FIG. 12 [D. M. Munroe, *A Lock-in Amplifier Primer*, EG & G Princeton Applied Research Technical Publ. T459 (1986); also: *Introduction to lock-in amplifiers*, Technical Note 115: Princeton Applied Research Corp. (1974); S. G. Letzter, Electron. Des. 21, 104 (1974); Brookdeal Electronics, *Introduction to lock-in amplifiers* (Bracknell, England), Technical Note 115; Stanford Research Systems Model SR850 DSP Lock-In Amplifier Manual, Sect. 3, (1992–1993)]. Since the output signal f(t) is periodic with period $T_o$ corresponding to reference angular frequency $\omega_o = 2\pi/T_o$, the output power SNR is given as (B. P. Lathi, *Random Signals and Communication Theory* (Int. Textbook Co., Scranton, Pa., 1968), Chaps. 1 and 4)

$$SNR = \frac{\text{Average Spectral Power of Signal Output}}{\text{Average Spectral Power of Noise Output}} = \frac{\overline{P(t)}}{\overline{P_n(t)}} \quad (33)$$

The experimental recorded SNR is simply the square root of the power SNR of Eq. (33). It is appropriate to use the mean-square value of the noise amplitude, since it is a random signal with zero mean value. The periodic output signal of repetition period $T_o$, $f_o(t)$, can be decomposed into a Fourier series.

Assuming a single first-order RC low-pass filter section of transfer function (M. L. Meade, *Lock-in amplifiers: principles and applications* [IEE Electrical Measurement Series 1, P. Peregrinus Ltd., Stevenage, Herts. England, 1983); D. M. Munroe, *A Lock-in Amplifier Primer*, EG & G Princeton Applied Research Technical Publ. T459 (1986); also: *Introduction to lock-in amplifiers*, Technical Note 115: Princeton Applied Research Corp. (1974)]

$$H(\omega) = \frac{1}{1 + i\omega\tau_{RC}} \quad (34)$$

keeps the treatment quite general, as various higher order filter gain roll-offs can be implemented by simple single filter section cascades using buffer amplifiers for isolation [M. L. Meade, *Lock-in amplifiers: principles and applications* (IEE Electrical Measurement Series 1, P. Peregrinus Ltd., Stevenage, Herts. England, 1983)]. Here $\tau_{RC} = RC$ (R: resistance, C: capacitance of the filter). The impulse response of the filter is given by the inverse Fourier transform of Eq. (34).

$$h(t) = \frac{1}{\tau_{RC}} e^{-t/\tau_{RC}} u(t) \quad (35)$$

where u(t) is the unit step function. The filter output $f_{oT}(t)$ is the result of the convolution [B. P. Lathi, *Random Signals and Communication Theory* (Int. Textbook Co., Scranton, Pa., 1968), Chaps. 1 and 4]

$$f_{oT}(t) = \int_{-\infty}^{\infty} h(t-\zeta)f_i(\zeta)d\zeta = \frac{e^{-t/\tau_{RC}}}{\tau_{RC}} \int_0^\infty f_i(\zeta) e^{\zeta/\tau_{RC}} d\zeta \quad (36)$$

Since the input signal is periodic with period $T_o$, and the LIA filter time constant is usually experimentally set to be very long, $\tau_{RC} \gg T_o$, expanding the exponentials in Eq. (36) yields:

$$f_{oT}(t) = f_{oT}(T_o) = \frac{1}{T_o} \int_0^{T_o} f_i(\zeta)d\zeta \quad (37)$$

Figure 12:
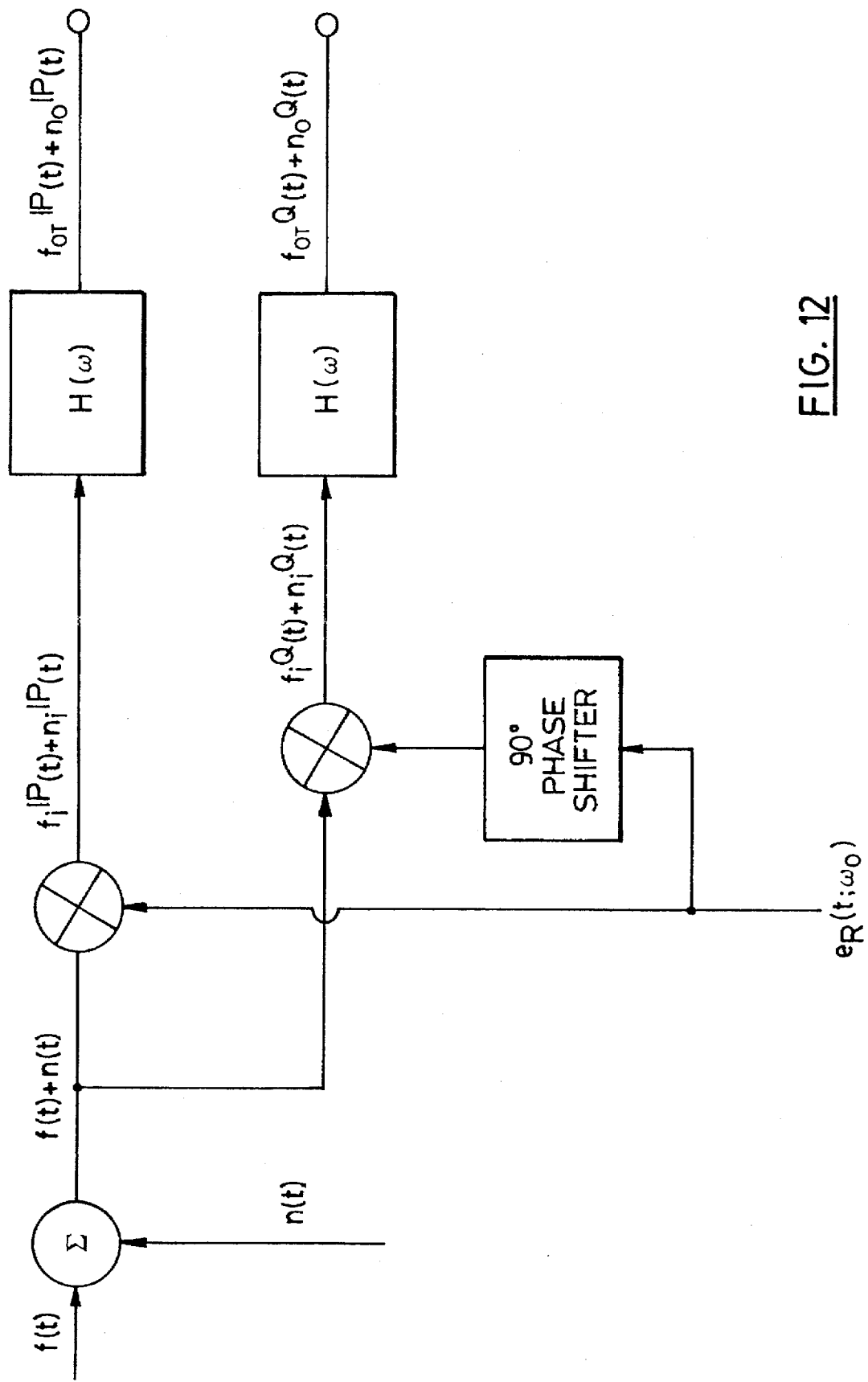
FIG. 12 is the layout of transient signal pathway through a lock-in amplifier (LIA) where the various symbols are defined in the text, $\Sigma$ stands for summing stage and x stands for mixing (multiplying) stage.

At this point it should be remembered that $f_i(t)$ is the output of the IP or Q mixer stage, FIG. 12. Therefore, it consists of the product of the input transient waveform f(t) and the reference waveform $e_R(t;\omega_o)$. Depending on the type of LIA used, two reference waveforms can be considered. In digital instruments the reference is a pure sine wave synthesized digitally. In analog instruments a square wave reference signal is used.

For digital LIA's Equation (37) may be written $$f_{oT}^{(IP,Q)}(T_o) = \frac{1}{T_o} \int_0^{T_o} f(\zeta) e_R^{(IP,Q)}(\zeta; \omega_o) d\zeta \quad (38)$$

for either IP or Q signal channel, where $$e_R^{IP}(t;\omega_o) = \cos(\omega_o t) \quad (39)$$

$$e_R^{Q}(t;\omega_o) = \sin(\omega_o t) \quad (39)$$

The repetitive input transient f(t) may be expanded in a real Fourier series:

$$f(t) = \frac{1}{2} a_o + \sum_{n=1}^{\infty} [a_n \cos(n\omega_o t) + b_n \sin(n\omega_o t)] \quad (40a)$$

with the Fourier coefficients $$a_n(\omega_o) = \frac{\omega_o}{\pi} \int_0^{T_o} f(t)\cos(n\omega_o t)dt \quad (40b)$$

and $$b_n(\omega_o) = \frac{\omega_o}{\pi} \int_0^{T_o} f(t)\sin(n\omega_o t)dt \quad (40c)$$

The orthogonality property of the basis functions {cos($n\omega_o t$)} and {sin($n\omega_o t$)} yields upon combination of Eqs. (38)–(40):

$$f_{oT}^{(IP,Q)}(\omega_o) = \frac{1}{2} \begin{bmatrix} a_1(\omega_o) \\ b_1(\omega_o) \end{bmatrix} \quad (41)$$

Equation (41) may be used to calculate the average output spectral power [B. P. Lathi, *Random Signals and Communication Theory* (Int. Textbook Co., Scranton, Pa., 1968), Chaps. 1 and 4]:

$$\overline{P}^{(IP,Q)}(\omega_o) = \frac{1}{8} \begin{bmatrix} |a_1(\omega_o)|^2 \\ |b_1(\omega_o)|^2 \end{bmatrix} [W] \quad (42)$$

It is important to note that the signal output from a digital lock-in amplifier contains no harmonic components, precisely due to the purely sinusoidal reference. This is an advantage, because it eliminates noise contributions from harmonic responses, compared to analog LIAs. Generally, the SNR from digital LIAs can be shown to be greater than that of analog LIAs.

b. Lock-in Amplifier Output Noise

The most commonly encountered noise in instrumentation systems is the so-called Gaussian noise. This type of noise is characterized by zero mean and a Gaussian probability density function. Considering a LIA output noise signal $n_o(t)$ with power spectral density $S_n(\omega)$, we may conveniently represent [B. P. Lathi, *Modern Digital and Analog Communication Systems* (Holt, Rinehart and Winston, New York, 1983), Chap. 2.10] n(t) as the limit of a sum of sinusoids of frequency $\Delta f$ apart over its frequency spectrum, when $\Delta f \to 0$. Therefore, $$n(t) = \lim_{\Delta\omega \to 0} \sum_{j=-\infty}^{\infty} C_j \cos(\omega_j t + \theta_j); \omega_j = j\Delta\omega \quad (43)$$

where the Fourier coefficient $C_j$ is to be determined. Upon passage through the LIA filter of transfer function $H(\omega)$, the mean-square value of the output noise is $$\overline{n_o^2(t)} = \frac{1}{2\pi} \int_{-\infty}^{\infty} S_n(\omega) |H(\omega)|^2 d\omega \quad (44)$$

Figure 13:
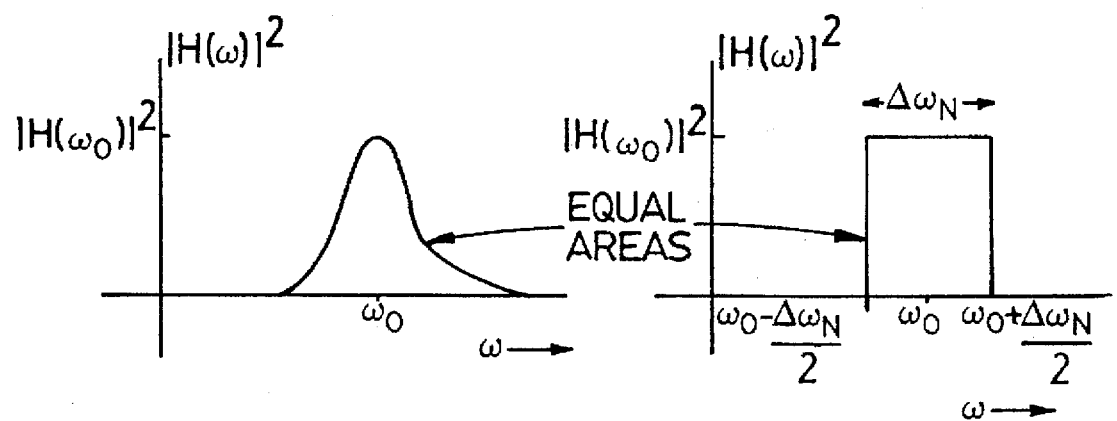
FIG. 13 is the definition of the equivalent Noise Bandwidth (ENBW) of the LIA.

Since $n_o(t)$ is a stationary process, its mean-square value is independent of t. For each Fourier component of $n_o(t)$, a treatment similar to that of the periodic output signal $f_o(t)$, gives:

$$\overline{n_o^2(t)} = \frac{1}{8} \lim_{\Delta\omega \to 0} \sum_{j=-\infty}^{\infty} C_j^2 [|H(\omega_o - \omega_j)|^2 + |H(\omega_o + \omega_j)|^2] \quad (45)$$

where H is the low-pass filter transfer function. Henceforth it is convenient to define the Equivalent Noise Bandwidth (ENBW) $\Delta\omega_N = 2\pi\Delta f_N$ as in FIG. 13. The ENBW is an ideal bandpass filter of constant gain $H(\omega_o)$ which delivers the same root-mean-square value of the noise signal power as the actual LIA output:

$$\Delta\omega_N = \frac{1}{|H(\omega_o)|^2} \int_0^{\infty} |H(\omega)|^2 d\omega \quad (46a)$$

where $$H(\omega_o) = \begin{cases} 1 \; ; \omega_o - (\Delta\omega_N/2) < \omega_o < \omega_o + (\Delta\omega_N/2) \\ 0 \; ; \text{otherwise} \end{cases} \quad (46b)$$

The LIA output noise power is $$\overline{P}_n = \overline{n_o^2(t)}\Delta\omega_j [W] \quad (47)$$

Upon replacement of all the individual noise frequency bands $\Delta\omega_j = j\Delta\omega$ by suitable ENBWs, such that from Eq. (46a), one may write:

$$|H(\omega_j)|^2 \Delta\omega_j = \int_0^{\infty} |H(\omega)|^2 d\omega. \quad (48)$$

One obtains for the output noise power from Eqs. (45), (47) and (48) and from the assumption of white noise (e.g. thermal or Johnson noise):

$$\overline{P}_n = \left(\frac{N}{4\pi}\right) \Delta\omega_N \quad (49)$$

for the IP or Q channel output noise of the LIA. Here N is the (assumed constant) noise power density [W/Hz][S. Haykin, *An Introduction to Analog and Digital Communications* (J. Wiley & Sons, New York, 1989), p. 160].

c. Photothermal SNRs
1. Harmonic Thermal-Wave (FD) Mode

Figure 14:
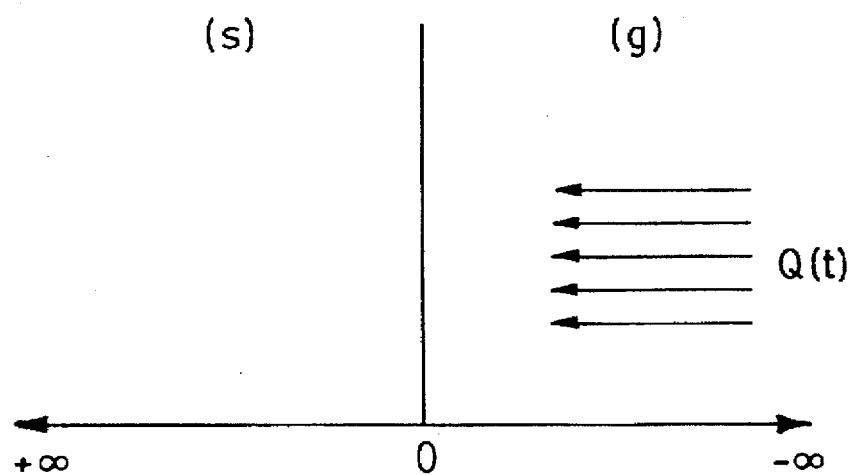
FIG. 14 shows a one-dimensional, semi-infinite photothermal geometry. (s): solid, (g): gas, Q(t): time-dependent incident photothermal intensity.

For simplicity we shall consider a semi-infinite solid geometry as shown in FIG. 14. For harmonically modulated incident intensity (frequency domain (FD) mode):

$$Q(t) = \frac{Q_o}{2}[1 + \cos(\omega_o t)] \quad (50)$$

a simple heat conduction calculation with boundary conditions of temperature and heat flux continuity [H. S. Carslaw and J. C. Jaeger, *Conduction of Heat in Solids*, 2nd Ed. (Oxford, 1965), Chap. 2.6] gives for the thermal-wave field in the solid $$T_s(x,t) = \frac{Q_o}{4k_s\sigma_s(1+b_{qs})} e^{-\sigma_s x + i\omega_o t} \quad (51)$$

Here $k_s$ is the solid thermal conductivity; $b_{gs}$ is the ratio of the thermal effusivities of gas and solid, $b_{gs} = e_g/e_s$; and $\sigma_s = (1+i)\sqrt{\omega_o/2\alpha_s}$, where $\alpha_s$ is the solid thermal diffusivity. Let us assume an experimental situation which is capable of monitoring the surface temperature oscillation of the solid directly, such as infrared photothermal radiometry [Z. Chen and A. Mandelis, Phys. Rev. B15 46, 13526 (1992-II); W. P. Leung and A. C. Tam, J. Appl. Phys. 56, 153 (1984)]:

$$T_s(0,t) = \frac{A}{\sqrt{\omega_o}} \cos\left(\omega_o t - \frac{\pi}{4}\right) = f(t) \quad (52a)$$

where $$A \equiv \frac{K_i Q_o}{4e_s(1+b_{qs})} \quad (52b)$$

and $K_i$ is an instrumental constant dependent on detection geometry. $K_1$ does not change upon changing the input thermal modulation waveform of the system. In Equation (52a) $T_s(O, t)$ may be identified as the input signal f(t) to the LIA.

Computation of the fundamental Fourier coefficients of the FD surface temperature expression, Eq. (52a), via Eqs. (40b,c) and insertion into the expression for the average output spectral power, Eq. (49), with the average output noise power $\overline{P}_n$, Eq. (49), yields $$a_1(\omega_o) = b_1(\omega_o) = \frac{A}{\sqrt{2\omega_o}} \quad (53)$$

Therefore, for both IP and Q channels:

$$SNR^{FD}(\omega_o) = \left(\frac{|A|^2}{8N\Delta f_N}\right) \frac{1}{\omega_o} \quad (54)$$

The output power SNR in this mode decreases inversely proportional to the radiation intensity modulation frequency, a well-known experimental fact.

2. Rate-Window (RW) Photothermal Mode

For an absolute and useful comparison of SNRs, the identical instrumental and sample configuration to that above is considered. In this mode, however, a time-gated optical pulse is incident on the sample surface of FIG. 14. The pulse is repetitive with period $T_o = 2\pi/\omega_o$. The modulated incident intensity can be described by a rectangular pulse:

$$Q(t) = \begin{cases} Q_o \; ; 0 < t < \tau_p \\ 0 \; ; \tau_p < t < T_o \end{cases} \quad (55)$$

A simple heat conduction calculation in Laplace space with the same boundary conditions as the harmonic thermal-wave problem of Sect. IV-A and initial condition $T_s(0, x) = 0$ gives the TD counterpart of Eq. (52):

$$T_s(0,t) = \frac{4}{\sqrt{\pi}} A \times \begin{cases} \sqrt{t} \; ; 0 \leq t \leq \tau_p \\ \sqrt{t} - \sqrt{t-\tau_p} \; ; \tau_p \leq t \leq T_o \end{cases} \quad (56)$$

A is given in Eq. (52b). Calculation of the fundamental Fourier coefficients of the function $f(t) = T_s(0, t)$ gives $$a_1(\omega_o) = \frac{4\omega_o A}{\pi^{3/2}} \left[ \int_o^{\tau_p} \sqrt{t}\, \sin(\omega_o t) dt + \int_{\tau_p}^{T_o} (\sqrt{t} - \sqrt{t-\tau_p})\cos(\omega_o t) dt \right] \quad (57)$$

$$= -\frac{4A}{\pi\sqrt{2\omega_o}} \left\{ S(2) - \left[ \sqrt{\frac{2}{\pi}(2\pi - \omega_o \tau_p)} \right] \cos(\omega_o \tau_p) - \right.$$

$$\left. C\left[ \sqrt{\frac{2}{\pi}(2\pi - \omega_o \tau_o)} \right] \sin(\omega_o \tau_p) + \sqrt{\frac{2}{\pi}(2\pi - \omega_o \tau_p)}\, \sin(\omega_o \tau_o)\cos(\omega_o \tau_p) \right\}$$

$$b_1(\omega_o) = \frac{4\omega_o A}{\pi^{3/2}} \left[ \int_o^{\tau_p} \sqrt{t}\, \sin(\omega_o t) dt + \int_{\tau_p}^{T_o} (\sqrt{t} - \sqrt{t-\tau_p})\sin(\omega_o t) dt \right] \quad (58)$$

$$= \frac{4A}{\pi\sqrt{2\omega_o}} \left\{ C(2) - C\left[ \sqrt{\frac{2}{\pi}(2\pi - \omega_o \tau_p)} \right] \cos(\omega_o \tau_p) + \right.$$

$$\left. S\left[ \sqrt{\frac{2}{\pi}(2\pi - \omega_o \tau_p)} \right] \sin(\omega_o \tau_p) + \sqrt{\frac{2}{\pi}(2\pi - \omega_o \tau_p)}\, \sin^2(\omega_o \tau_p) \right\}$$

where $$S(x) \equiv \frac{1}{\sqrt{2\pi}} \int_o^{\frac{\pi}{2} x^2} \frac{\sin y}{\sqrt{y}} dy \quad (59a)$$

$$C(x) \equiv \frac{1}{\sqrt{2\pi}} \int_o^{\frac{\pi}{2} x^2} \frac{\cos y}{\sqrt{y}} dy. \quad (59b)$$

Two rate-window photothermal modes are possible: pulse repetition period, $T_o$, scan with fixed $\tau_p$; and pulse duration, $\tau_p$, scan with fixed $T_o$. In both scans extrema of the photothermal signal occur. SNR comparisons with the FD mode are most easily made by considering the $\tau_p/T_o$ ratio in the rate-window method which yields an SNR equal to that of FD method. If $\omega_o \tau_p \ll 2\pi$, i.e. for $\tau_p \ll T_o$, the following approximations may be made:

$$S\left[ \sqrt{\frac{2}{\pi}(2\pi - \omega_o \tau_p)} \right] \simeq S(2) \quad (60)$$

$$C\left[ \sqrt{\frac{2}{\pi}(2\pi - \omega_o \tau_p)} \right] \simeq C(2) \quad (61)$$

$$\cos(\omega_o \tau_p) \simeq 1;\ \sin(\omega_o \tau_p) \simeq \omega_o \tau_p \quad (62)$$

Therefore, Eq. (57) becomes for $\tau_p \ll T_o$:

$$|a_1(\omega_o)| \simeq \frac{4A[2 - C(2)]}{\pi\sqrt{2\omega_o}} (\omega_o \tau_p) \quad (63)$$

Since the instrumental configuration remains identical to the FD LIA method, the IP and Q channel output noise power $\overline{P}_n$ remains the same and is given by Eq. (49). Inserting [M. Abramowitz and A. Stegun, *Handbook of Mathematical Functions*, 9th ed., (National Bureau of Standards, Washington, D.C. 1970)] $C(2) \simeq 0.488$ in Eq. (63) one obtains $$SNR^{RWJP}(\omega_o) = \left( \frac{4[2 - C(2)]}{\pi} \right)^2 \left[ \frac{|A|^2(\omega_o \tau_p)^2}{8N\Delta f_N} \right] \frac{1}{\omega_o} \quad (64a)$$

$$= 3.706(\omega_o \tau_p)^2 \left( \frac{|A|^2}{8N\Delta f_N} \right) \frac{1}{\omega_o} \quad (64b)$$

Equation (64) indicates that the output SNR from a rate-window photothermal experiment with fixed pulse duration and scanned repetition period or vice-versa is higher than the respective FD scan SNR, Eq. (54) when $$3.706(\omega_o \tau_p)^2 \geq 1 \Rightarrow \tau_p \geq 8.267 \times 10^{-2} T_o, \quad (65)$$

i.e. the in-phase rate-window method outperforms the conventional FD mode if the pulse duration is greater than 8.27% of the repetition period. The SNR advantage of the rate-window method over the FD method at common $\omega_o$ increases with increasing modulation frequency, Eq. (64). This fact suggests that the rate-window approach should be favoured in situations where fast photothermal detection is required, such as with responses of thin, thermally conducting layers. A similar calculation to the IP case may be carried out for the Q-channel of the LIA, giving from Eq. (58) in the limit $\omega_o \tau_p \ll 2\pi$:

$$SNR^{RW,Q}(\omega_o) \simeq \left[ \frac{4S(2)}{\pi} \right]^2 \left[ \frac{|A|^2(\omega_o \tau_p)^2}{8N\Delta f_N} \right] \frac{1}{\omega_o} \quad (66a)$$

$$= 0.191(\omega_o \tau_p)^2 \left( \frac{|A|^2}{8N\Delta f_N} \right) \frac{1}{\omega_o} \quad (66b)$$

The condition for SNR advantage of the Q-channel rate-window scan over the FD method at the same frequency here is more stringent than the IP condition, yet easy to achieve experimentally:

$$0.191(\omega_o \tau_p)^2 \geq 1 \Rightarrow \tau_p \geq 0.364 T_o \quad (67)$$

In the foregoing experimental examples, the SNRs of both FD and rate-window modes decrease substantially with increasing frequency, owing to their $\omega_o^{-1}$ dependence. If the pulse repetition period is fixed (i.e. $\omega_o$ is fixed) and $\tau_p$ is scanned, then the relative in-phase SNR becomes $$\rho \equiv \frac{SNR^{RWJP}(\omega_o)}{SNR^{FD}(\omega_o)} = \left(\frac{4[2-C(2)]}{\pi}\right)^2 (\omega_o\tau_p)^2 = 3.706(\omega_o\tau_p)^2 \quad (68)$$

assuming $\omega_o\tau_p \ll 1$, and $$\rho = \left(\frac{4[S(2)+S(\sqrt{2})]}{\pi}\right)^2 = 1.81 \quad (69)$$

for $\tau_p = T_o/2$ (rate-window with 50% duty cycle). Similar SNR advantages are enjoyed by the LIA Q-channel as well.

The advantage of pulse-duration-scanned rate-window over FD photothermal measurements lies not only on the high SNR due to the rate-window process itself as shown in Eqs. (68) and (69), but also in comparison with the $T_o$-scanned rate-window. This is so, because $T_o$ scanning is equivalent to increasing the modulation frequency, which compromises the photothermal SNR. To illustrate this important difference between the two rate-window scanning modes, consider the ratio of their SNRs from Eq. (64b) under the condition $\tau_p \ll T_o$:

$$\rho \equiv \frac{SNR^{RW(IPorQ)}(\tau_p,\omega_o^*)}{SNR^{PWJP}(\tau_p^*,\omega_o)} = \frac{\omega_o}{\omega_o^*}\left(\frac{\omega_o^*\tau_p}{\omega_o\tau_p^*}\right)^2 = \quad (70)$$

$$\frac{T_o^*}{T_o}\left[\frac{(\tau_p/T_o^*)^2}{(\tau_p^*/T_o)^2}\right]$$

In Equation (70) starred quantities denote fixed parameters; unstarred quantities denote scanned parameters. It can be seen that for $\tau_p$-scanned rate-window, the ratio $\tau_p/T_o^*$ increases with increasing $\tau_p$. Similarly, for $T_o$-scanned rate-window the ratio $\tau_p^*/T_o$ increases with decreasing $T_o$. Assuming equal rates of increase, we obtain $$\rho = T_o^*/T_o \quad (71)$$

Note that always $\rho \geq 1$, the equality sign holding when both scans commence with the same $\tau_p$ and $T_o$. Then $\rho$ quickly increases as $\tau_p$ increases (in constant $T_o^*$ mode) or as $T_o$ decreases (in constant $\tau_p^*$ mode). FIG. 8 shows the dramatic SNR enhancement in the Q-channel $\tau_p$-scanned mode and should be compared to FIG. 7 which represents the $T_o$-scanned mode.

3. Pulsed and Time-Averaged Photothermal (TD) Mode

Pulsed photothermal (time-domain, TD) experiments are in widespread use owing to the ease of interpretation of the data and the ability to excite and monitor fast and ultrafast photothermal phenomena using pulsed lasers. The rate-window mode is principally a transient signal detection method using synchronous demodulation, therefore, the question of the SNR of the time-averaged pulsed photothermal method arises when direct comparison of the two measurement techniques is to be made. In this case the transient repetitive output signal, $f_o(t)$, may be considered to be the result of averaging a continuous random variable time-dependent function. The mean value of the function $f_o(t)$ is [B. P. Lathi, *Random Signals and Communication Theory* (Int. Textbook Co., Scranton, Pa., 1968), Chaps. 1 and 4]

$$E[f_o(t)] \equiv \overline{f_o(t)} = \int_{-\infty}^{\infty} f_o(t)p(f_o;t)df_o \quad (72)$$

If $m_i$ represents the number of times the function $f_o(t)$ takes on the value $f_{oi}$, and n is the total number of times the transient experiment is repeated, then formally $p(f_o; t)$ is the limit as $n\to\infty$ of the ratio $m_i/n$; physically $p(f_o; t)$ is a probability density. The variance of $f_o(t)$ at any instant, t, is given by:

$$\sigma_{f_o}(t) = \sqrt{\overline{f_o^2(t)} - [\overline{f_o(t)}]^2} \quad (73)$$

In a pulsed photothermal experiment the co-added repetitive pulses are not narrow-band filtered, since they are not transmitted through a LIA. Assuming stationary Gaussian white noise dominating all other types of noise, the mean-square value of the noise signal can be expressed as in Eq. (44), which takes on the particularly simple form:

$$\overline{n_o^2(t)} = \frac{N}{4\pi}\int_{-\infty}^{\infty} |H(\omega)|^2 d\omega. \quad (74)$$

$H(\omega)$ denotes the transfer function of the dominant frequency-limiting mechanism of the experiment, which acts as a distributed band-pass filter. The probability density function of band-limited Gaussian white noise is known to be [B. P. Lathi, *Random Signals and Communication Theory* (Int. Textbook Co., Scranton, Pa., 1968), Chaps. 1 and 4]

$$p(n_o) = \frac{1}{\sqrt{2\pi NB}} e^{-n_o^2/2NB} \quad (75)$$

where B is the effective bandwidth:

$$B = \frac{W}{2\pi} \; [Hz] \quad (76)$$

Here W is the entire bandwidth of the experimental frequency spectrum. For repetitive pulsed photothermal transients with repetition period $T_o$, the bandwidth is $|\omega| < \omega_o = 2\pi/T_o$, which yields:

$$B = \frac{1}{T_o} = \frac{\omega_o}{2\pi} \quad (77)$$

The output signal is mixed with white Gaussian noise of zero mean value:

$$r_o(t) = f_o(t) + n_o(t) \quad (78)$$

where, according to Eqs. (72) and (73):

$$\overline{n_o^2(t)} = \int_{-\infty}^{\infty} n_o^2 p(n_o)dn_o = NB \quad (79)$$

Now let $f_o(t)$ be given by the photothermal response of a semi-infinite solid to a rectangular pulse Q(t). This response is described by Eq. (56). Given that $r_o(t)$ is considered a random function over an ensemble with Gaussian probability density, that probability density may be described using Eq. (75) with $n_o = r_o - f_o$:

$$p(r_o; f_o) = \frac{1}{\sqrt{2\pi NB}} e^{-(r_o-f_o)^2/2NB} \quad (80)$$

After infinite time-averaging of the repetitive transient signals, the mean value of the resulting TD signal will be $$\overline{r_o(t)} = \int_{-\infty}^{\infty} r_o p(r_o; f_o) dr_o = f_o(t) \quad (81)$$

where Eq. (80) was used for the calculation.

The system output noise will result in a variance which determines the SNR. This variance is given by Eq. (73) upon replacing $f_o$ by $r_o$:

$$\sigma_{r_o}^2 = \int_{-\infty}^{\infty} r_o^2 p(r_o; f_o) dr_o - \left[ \int_{-\infty}^{\infty} r_o p(r_o; f_o) dr_o \right]^2 \quad (82)$$

$$= [NB + f_o^2(t)] - f_o^2(t) = NB$$

From Equations (81) and (82) we conclude [see also M. L. Meade, *Lock-in amplifiers: principles and applications* (IEE Electrical Measurement Series 1, P. Peregrinus Ltd., Stevenage, Herts. England, 1983), Appendix 2]:

$$SNR^{TD}(t) = \frac{\overline{r_o^2(t)}}{\overline{n_o^2(t)}} = \frac{f_o^2(t)}{\sigma_{r_o}^2} = \frac{T_s^2(0,t)}{NB} \quad (83)$$

Over the entire repetition cycle, the output power SNR is given as follows:

$$SNR^{TD}(T_o) = \frac{\frac{1}{T_o} \int_0^{T_o} T_s^2(0,t) dt}{NB} \quad (84)$$

Now calculation of the integral in the numerator using Eq. (56) and I. S. Gradshteyn and I. M. Ryzhik, *Table of Integrals, Series, and Products* (Academic, New York, 1980), entries 2.261 and 2.262.3, gives $$SNR^{TD}(T_o) = \left[ T_o + \frac{1}{2} \frac{\tau_p^2}{T_o} - \tau_p - \right. \quad (85)$$

$$\sqrt{T_o^2 - \tau_p T_o} \left( 1 - \frac{\tau_p}{2T_o} \right) +$$

$$\left. \frac{\tau_p^2}{2T_o} \ln\left( \sqrt{\frac{T_o}{\tau_p}} + \sqrt{\frac{T_o}{\tau_p} - 1} \right) \right] \left( \frac{16 A^2}{\pi NB} \right)$$

This SNR increases with increasing $\tau_p$, as expected since the total energy imparted into the sample thus increases. For a direct comparison with the rate-window SNR, Eq. (64), consider the case of a short laser pulse, such that $\tau_p \ll T_o$. Using the approximations $$(T_o^2 - \tau_p T_o)^{1/2} \simeq T_o \left( 1 - \frac{\tau_p}{2T_o} \right) \quad (86)$$

and $$\tau_p^2 \ln\left( \sqrt{\frac{T_o}{\tau_p}} + \sqrt{\frac{T_o}{\tau_p} - 1} \right) \simeq \quad (87)$$

$$\tau_p^2 \ln\left( 2\sqrt{\frac{T_o}{\tau_p}} \right) \simeq \frac{\tau_p^{5/2}}{2\sqrt{T_o}}$$

and keeping in mind Eq. (77), we obtain:

$$SNR^{TD}(\tau_p \ll T_o) \simeq \frac{4 A^2}{\pi NB} \left( \frac{\tau_p^2}{T_o} \right) = \quad (88)$$

$$\frac{4 A^2 \tau_p^2}{\pi N} \quad ; \quad (A = |A|^2)$$

Finally, using Eqs. (64b) and (88) the relative SNR for short optical pulses $\tau_p \ll T_o$ becomes:

$$\frac{SNR^{RWJP}(\omega_o)}{SNR^{TD}(T_o)} = 2.29 \left( \frac{\omega_o}{\Delta \omega_N} \right) \gg 1 \quad (89)$$

Figure 15A:
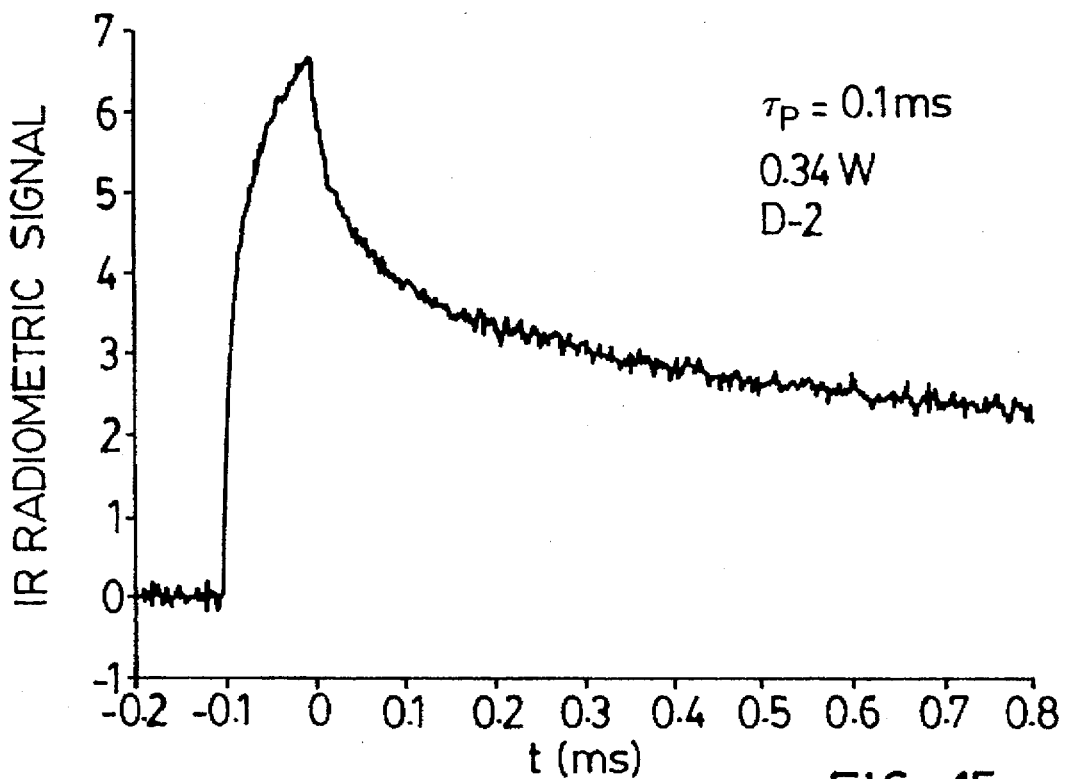
FIG. 15a is the backscattered infrared photothermal radiometric transient (time domain, TD) signal from a diamond specimen averaged over N=5000 measurement samples using a pulse duration $\tau_p$=0.1 ms and laser power $Q_o$=0.34 W.
Figure 15B:
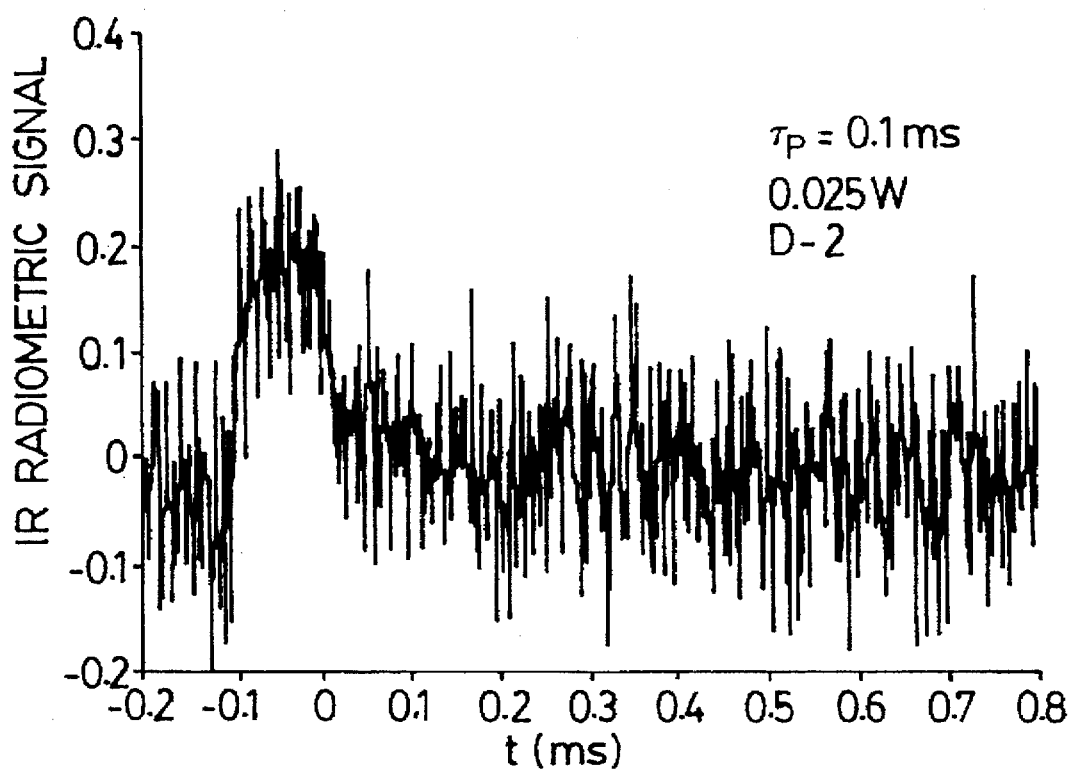
FIG. 15b is the same as FIG. 12a except that the laser power is $Q_o$=25 mW.
Figure 16:
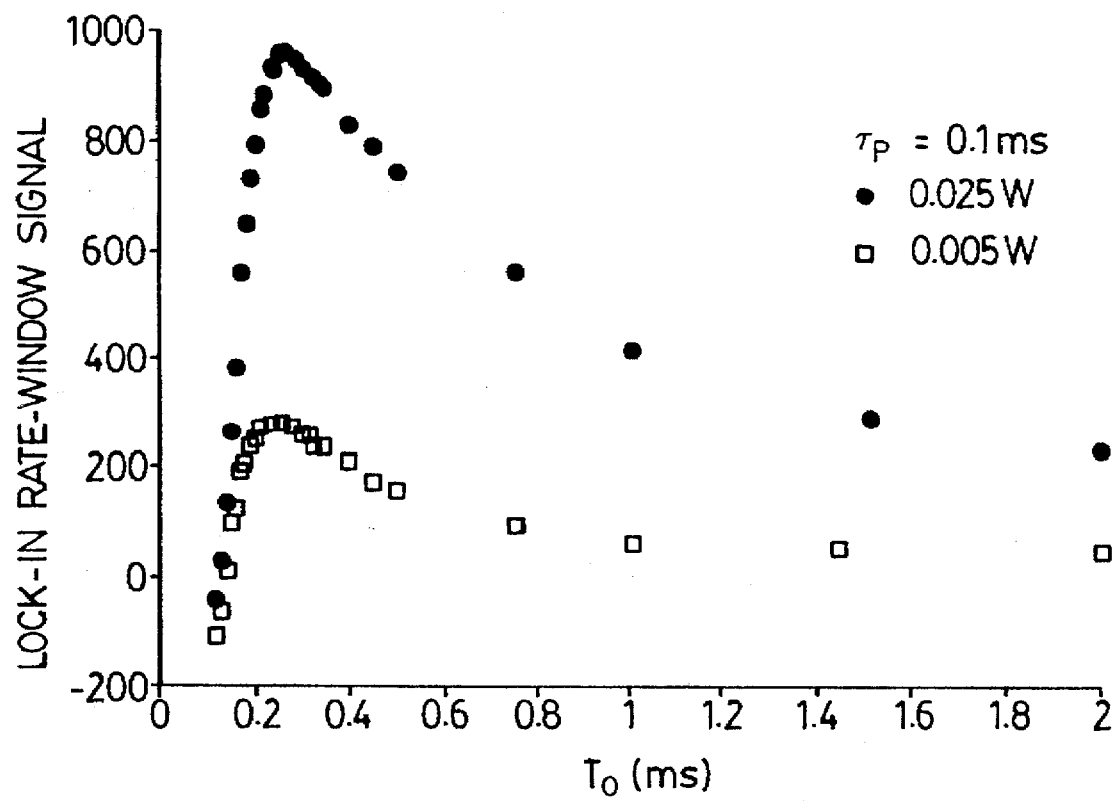
FIG. 16 is the analog LIA in-phase (IP) -channel infrared photothermal radiometric rate-window signals from the diamond of FIG. 15, wherein two scans were performed with $\tau_p$=0.1 ms and $Q_o$=25 mW (black dots) and 5 mW (squares).

This ratio is normally much grater than one, due to the extremely narrow ENBW's afforded by LIAs [typically $\Delta f_N \simeq 0.01$ Hz at $f_o = \omega_o/2\pi = 10$ kHz], (Stanford Research Systems Model SR850 DSP Lock-In Amplifier Manual, Sect. 3, (1992–1993)]. This advantage of rate-window detection over the co-added transient method is demonstrated experimentally in FIGS. 15 and 16. FIG. 15 shows a photothermal infrared radiometric transient measured from a diamond sample using a finite duration laser pulse ($\tau_p = 0.1$ ms) and two levels of incident irradiance. The low incident laser power is only 25 mW, FIG. 15b. Several thousand repetitive signal transients were co-added. FIG. 16 shows the LIA rate-window scans measured with the same $\tau_p$ and the incident laser power of FIG. 15b, as well as an even lower power of only 5 mW. No transient signal could be registered in the transient scope in this latter case, even after the co-addition and averaging of several thousand pulses. Comparison of FIGS. 15b and 16 clearly indicates the superior SNR of the LIA rate-window method.

It should be kept mind that in the foregoing one-dimensional, single-ended, back-scattered photothermal approach it is necessary to choose the right frequency (or repetition period) range such that the sample is thermally thin, in order to determine the diffusivity of the material. In the frequency scan method, it is the range where the extremum occurs. In the rate-window method the right range is not so obvious from the in-phase or quadrature data. It is therefore necessary to check the signal phase at the 50% duty cycle point to ascertain thermal thinness, using as the criterion the deviation from the semi-infinite reference sample signal phase (–45°), see A. Rosencwaig and A. Gersho, J. Appl. Phys. 47, 64 (1976).

It is possible to use a focused laser beam and monitor the temperature away from the heated spot on the same surface where three dimensional heat flow has to be taken into consideration. In this case the sample may be of any thickness which does not have to be known but the theoretical analysis is less straightforward.

In summary, there is provided a dynamic, noncontact method of characterizing the thermal and electronic properties of solids. In particular, there is provided a dynamic method of measuring thermal diffusivity of solids, particularly thin solids having short thermal transport times or electronic transport, or defect properties of electronic (semiconductor) substrates and devices. The method of measuring thermal diffusivities, termed the lock-in photothermal rate window method, involves irradiating a sample surface with a repetitive square laser pulse of duration $\tau_p$ and period $T_0$ and monitoring the temperature profile by measuring the infrared radiation emitted from the sample surface. The period $T_0$ of the repetitive heating pulse is maintained constant and the pulse duration $\tau_p$ is varied in the range between 0 and $T_0$ with the temperature measured at each value of $\tau_p$. The method of measuring electron-hole recombination lifetimes in semiconductors, termed rate-window photothermal infrared radiometry, (RW-PTR), involves irradiating a sample surface in a manner similar to the foregoing photothermal rate window method and scanning either the period $T_0$ or the duration $\tau_p$ of the repetitive laser pulse (one of the two parameters remaining constant) and monitoring the blackbody emission profile from the sample surface. The method of measuring defect or contaminant states and concentrations in semiconductors, termed photothermal radiometric deep-level transient spectroscopy (PTR-DLTS), involves irradiating the sample surface with a repetitive square laser pulse of duration $\tau_p$ and period $T_0$ (both fixed) and monitoring the blackbody emission profile as the sample temperature is scanned. A plot of the thermally stimulated photothermal signal as a function of temperature gives rise to a curve ("spectrum") with a maximum at a particular temperature, from which electronic trap parameters related to native or process-induced defects can be derived.

The photothermal signal in all the foregoing methods is input into a lock-in amplifier which measures the fundamental Fourier component of the photothermal signal. The output of the lock-in amplifier is fitted to a theoretical model of the photothermal response of a repetitively irradiated sample to obtain the thermal diffusivity, or the recombination lifetime. The rate window method advantageously gives enhanced signal-to-noise ratio (SNR) for materials with very short thermal transport times such as metal foils compared to conventional frequency scanning methods.

The pulse duration-scanned rate-window method of measuring thermal diffusivities or recombination lifetimes is also advantageous over known methods since it does not require knowledge of the instrumental transfer function. The method disclosed herein is useful for in-situ, non-destructive monitoring of wear in quality control applications of engineered materials and electronic substrates/devices.

While the method of dynamically measuring thermal diffusivities of solids, excess carrier lifetimes and determining interbandgap energy levels in semiconductors forming the present invention has been described and illustrated with respect to the preferred apparatus and method embodiments disclosed herein, it will be appreciated that numerous variations of these methods may be made without departing from the scope of the invention.

Therefore what is claimed is:

1. A method of measurement of thermal diffusivity in a solid, comprising;
    (a) providing a sample of the solid;
    (b) irradiating the solid with an excitation pulse of repetition period $T_0$ and a pulse duration $\tau_p$, wherein a photothermal signal is responsively emitted from said solid;
    (c) detecting said emitted photothermal signal and inputting said photothermal signal into a signal detection means operable to measure a temporal fundamental Fourier component of said photothermal signal and to provide an output of said fundamental Fourier component; and
    (d) fitting said output fundamental Fourier component to a theoretical model of the photothermal response of the repetitively irradiated solid to calculate the thermal diffusivity.

2. The method according to claim 1 wherein said solid is a metal foil, wherein said excitation pulse is a periodic heat generating signal having the period $T_0$ to fixed and the pulse duration $\tau_p$ preselected in a range from about zero to $T_0$, wherein said signal detection means is a lock-in amplifier, processing said emitted photothermal signal to calculate a quadrature component of said fundamental Fourier component, and prior to detecting said photothermal signal the lock-in amplifier phase is tuned so that a phase of a signal from a homogeneous semi-infinite reference sample at a frequency of $1/T_0$ is about $-45°$, changing the pulse duration $\tau_p$ to a new value in said range and irradiating said metal foil and repeating steps (c) and (d) to obtain a corrected quadrature component for pulse durations $\tau_p$ spanning said range, wherein the theoretical model predicts the photothermal response of the heated metal foil from which the thermal diffusivity is obtained.

3. The method according to claim 1 wherein said solid is a semiconductor and said excitation pulse is a light pulse, one of either the pulse duration $\tau_p$ and the repetition period $T_0$ but not both are scanned while the other is maintained at a preselected value, the light pulse having a wavelength suitable to produce photoexcited electron and hole carriers, wherein after the light pulse is switched off recombination of said photoexcited electron and hole carriers occurs to release energy thereby causing a temporary increase in the temperature and infrared emissivity of the semiconductor responsively producing said photothermal signal.

4. The method according to claim 3 wherein said semiconductor has a preselected thickness and a thermal transit time across said thickness, and wherein said signal detection means is a lock-in amplifier, and wherein said repetition period $T_0$ is of the same order of magnitude as the thermal transit time of the semiconductor sample.

5. The method according to claim 4 wherein the repetition period $T_0$ is held at a preselected fixed value and the pulse duration $\tau_p$ is scanned in the range $0<\tau_p<T_0$.

6. The method according to claim 4 wherein the pulse duration $\tau_p$ is held fixed at about 1 ms and the repitition period $T_0$ is scanned at values $T_0>\tau_p$ responsively producing an extremum in said output signal.

7. A method of measuring thermal diffusivity of a solid, comprising the steps of:
    (a) providing a sample of the solid;
    (b) irradiating the solid with a periodic heat generating signal having a fixed period $T_0$ and a pulse duration $\tau_p$ in a range from about zero to $T_0$, wherein a photothermal signal is produced;
    (c) detecting said photothermal signal;
    (d) processing said photothermal signal using a signal processing means to measure a temporal fundamental Fourier component of the photothermal signal and to calculate a quadrature component of said fundamental Fourier component, and to correct said quadrature component for frequency dependent phase shifts due to said signal processing means to give an output quadrature value at said pulse duration $\tau_p$;
    (e) changing the pulse duration $\tau_p$ to a new value in said range and repeating steps (b) to (d) without further correcting for phase shifts;
    (f) repeating step (e) until said range has been scanned by the pulse duration $\tau_p$; and
    (g) fitting said output quadrature value to a theoretical model of the photothermal response of the repetitively irradiated solid to obtain the thermal diffusivity of the solid.

8. The method according to claim 7 wherein said sample is a metal foil having two opposed sides, wherein one of said two opposed sides is irradiated with said periodic heat generating signal and said photothermal signal is detected from said one side.

9. The method according to claim 7 wherein said sample is a metal foil having two opposed sides, wherein one of said two opposed sides is irradiated with said periodic heat generating signal and said photothermal signal is detected from the other side of the solid.

10. The method according to claim 7 wherein said photothermal signal is detected at a location spaced from said solid.

11. The method according to claim 7 wherein said signal processing means is a lock-in amplifier having a reference signal equal to $1/T_0$.

12. The method according to claim 7 wherein said signal processing means is a dual gate boxcar integrator having a gate spacing less than $T_0$.

13. The method according to claim 7 wherein said signal processing means is a lock-in amplifier, said lock-in amplifier has a phase, wherein prior to detecting said photothermal signal the lock-in amplifier phase is tuned so that a phase of a signal from a homogeneous semi-infinite reference sample at a frequency of $1/T_0$ is about $-45°$.

14. The method according to claim 7 wherein said periodic heat generating signal is a repetitive laser pulse of duration $\tau_p$ and period $T_0$.

15. A method of measurement of thermal diffusivity in a semiconductor having a charge carrier system, comprising;
   (a) providing a sample of the semiconductor;
   (b) irradiating the semiconductor with a light pulse having a pulse duration $\tau_p$ and repetition period $T_0$, wherein one of pulse duration $\tau_p$ and repetition period $T_0$ but not both are scanned while the other is maintained at a preselected value, the light pulse having a wavelength suitable to produce photoexcited electronic carriers, wherein after the light pulse is switched off recombination of said photoexcited electronic carriers occurs to release energy thereby causing a temporary increase in infrared emissivity and the temperature of the semiconductor responsively producing a photothermal signal;
   (c) detecting said photothermal signal and inputting said photothermal signal into a signal detection means to measure a temporal fundamental Fourier component of said photothermal signal and to provide an output signal; and
   (d) fitting said output signal to a theoretical model of the photothermal response of the repetitively irradiated semiconductor sample to obtain the thermal diffusivity of the semiconductor.

16. The method according to claim 15 wherein said semiconductor sample has a preselected thickness and a thermal transit time across said thickness, and wherein said signal detection means is a lock-in amplifier, and wherein said repetition period $T_0$ is preselected at about the same order of magnitude as the thermal transit time of the semiconductor sample.

17. The method according to claim 16 wherein the pulse duration $\tau_p$ is scanned in the range $0<\tau_p<T_0$.

18. The method according to claim 15 wherein the pulse duration $\tau_p$ is held fixed at about 1 ms and the repetition period $T_0$ is scanned at values $T_0>\tau_p$ responsively producing an extremum in said output signal.

19. The method according to claim 15 wherein said semiconductor sample has a preselected thickness and a thermal transit time across said thickness, and wherein said signal detection means is a boxcar integrator having dual time-gates which are set to less than the thermal transit time, and wherein the repetition period $T_0$ is fixed at about 3 of the thermal transit times and the pulse duration $\tau_p$ is scanned in the range $0<\tau_p<T_0$.

* * * * *